United States Patent [19]

Moriyama

[11] Patent Number: 5,695,449
[45] Date of Patent: Dec. 9, 1997

[54] COVER-SHEATHED ENDOSCOPE

[75] Inventor: Hiroki Moriyama, Yokohama, Japan

[73] Assignee: Olympus Optical Co., Ltd., Tokyo, Japan

[21] Appl. No.: 630,580

[22] Filed: Apr. 10, 1996

[30] Foreign Application Priority Data

Apr. 18, 1995 [JP] Japan .................. 7-092811

[51] Int. Cl.$^6$ .................. A61B 1/04
[52] U.S. Cl. .................. 600/122; 600/121
[58] Field of Search .................. 600/121, 122, 600/123, 124, 125, 133, 146, 147

[56] References Cited

U.S. PATENT DOCUMENTS

| | | | |
|---|---|---|---|
| 4,646,722 | 3/1987 | Silverstein et al. | 128/4 |
| 4,825,850 | 5/1989 | Opie et al. | 600/122 |
| 5,359,991 | 11/1994 | Takahashi et al. | 600/122 |
| 5,363,843 | 11/1994 | Danshevar | 600/122 X |
| 5,419,311 | 5/1995 | Yabe et al. | 128/4 |
| 5,431,150 | 7/1995 | Yabe et al. | 600/121 |
| 5,458,132 | 10/1995 | Yabe et al. | 600/121 |
| 5,458,133 | 10/1995 | Yabe et al. | 600/122 |
| 5,460,166 | 10/1995 | Yabe et al. | 600/121 |
| 5,460,167 | 10/1995 | Yabe et al. | 600/107 |
| 5,487,376 | 1/1996 | Yabe et al. | 600/121 |

*Primary Examiner*—Beverly M. Flanagan
*Attorney, Agent, or Firm*—David E. Dougherty

[57] ABSTRACT

An operating portion cover for covering an operating portion of a cover-sheathed endoscope is provided with a finger putting portion to which a finger of the operator can be put in order to operate a movable operating member such as a bending operation knob inside of the operating portion cover. The operator can easily operate the movable member by putting a finger to this operating finger putting portion.

32 Claims, 13 Drawing Sheets

COVER-SHEATHED ENDOSCOPE

BACKGROUND OF THE INVENTION

1. Field of the Invention

This invention relates to a cover-sheathed endoscope having an operating portion cover which covers at least an operating portion of an endoscope to be inserted into a living body.

2. Description of the Related Art

Recently, endoscopes are used broadly in the medical field and in the industrial field. Particularly in the medical field, because an endoscope is inserted into a living body, it is necessary to disinfect or sterilize the endoscope to surely prevent infections or the like.

Because a generally used disinfection treatment takes too much time decreasing the actual time for using the endoscope, a cover-sheathed endoscope used with a cover over it has been proposed.

As an example of a conventional operating portion cover for covering an operating portion of a cover-sheathed endoscope, U.S. Pat. No. 4,646,722 discloses that a cover for covering the whole operating portion is arranged over an inserting portion cover to cover the whole endoscope.

Such a cover for covering the whole operating portion is simple in shape. However, when operating an operating member which has a relatively large moveable area in the operating portion, such as a bending operation knob and a forceps upheaving operation knob, it is difficult to sufficiently move the operating member from the outside of the cover because the cover covers the operating members wholly.

Especially when operating a plurality of operating members alternately or simultaneously, such as a twist operation of up-and-down and left-and-right bending, the cover may be forcibly pulled or twisted, so that it may become difficult to move the operating member, or the cover is likely to be torn by an excessive force.

SUMMARY OF THE INVENTION

An object of this invention is to provide a cover-sheathed endoscope in which an operating member provided in its operating portion arranged inside an endoscope cover can be operated effectively as if an operating member of an endoscope not using an endoscope cover were operated.

Another object of this invention is to provide a cover-sheathed endoscope which enables smooth operation of an operating member, by providing an endoscope cover with a finger putting portion.

A further object of this invention is to provide a cover-sheathed endoscope which can be operated easily by providing an endoscope cover with a finger putting portion which can be manipulated by either the left hand or the right hand.

A further object of this invention is to provide a cover-sheathed endoscope which can be operated easily by providing an endoscope cover with a rotating cover.

A further object of this invention is to provide a cover-sheathed endoscope which can be operated easily by providing an endoscope cover with a knob cover.

A further object of this invention is to provide a cover-sheathed endoscope which provides a good feeling of gripping.

A feature of this invention is that an operating portion cover for covering an operating portion is provided with an operating finger putting portion via which a finger can be put to a movable operating member inside the cover, such as a bending operation knob, a forceps upheaving knob or the like.

According to this invention, a satisfying operation can be made without the cover being forcibly pulled or the cover coiling around the moveable operating member.

DETAILED DESCRIPTION OF THE PREFERRED EMBODIMENTS

Figure 1:
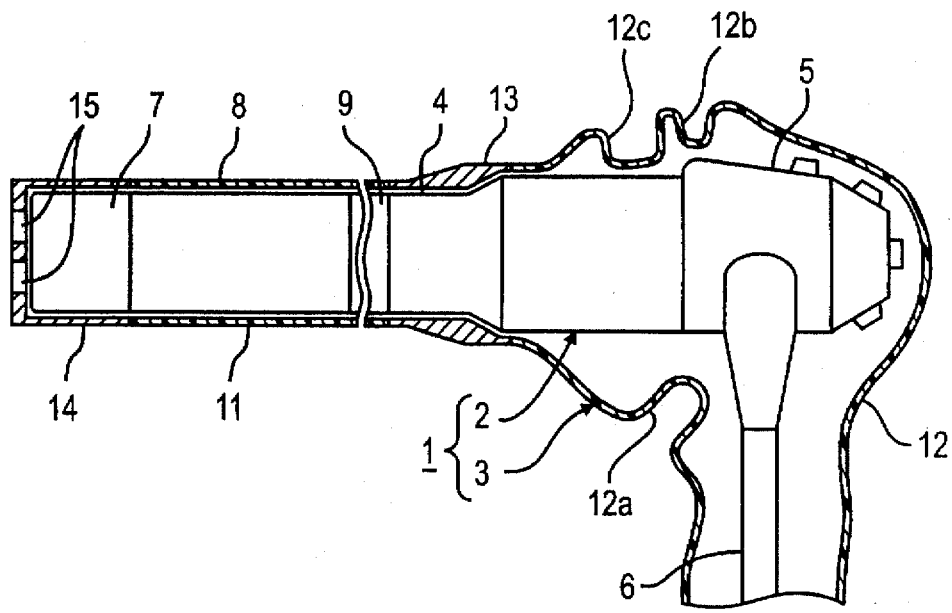
FIG. 1 is a schematic view of a cover-sheathed endoscope of a first embodiment of this invention.
Figure 2:
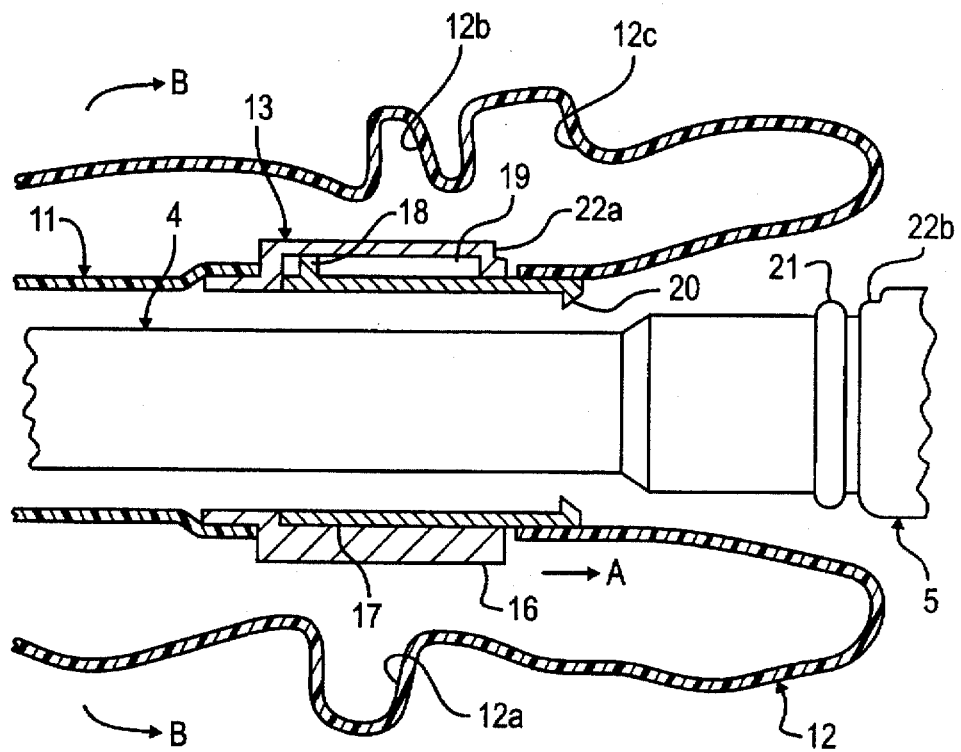
FIG. 2 is a cross-sectional view of the vicinity of a locking cap when an endoscope cover is attached to the cover-sheathed endoscope of the first embodiment of this invention.
Figure 3:
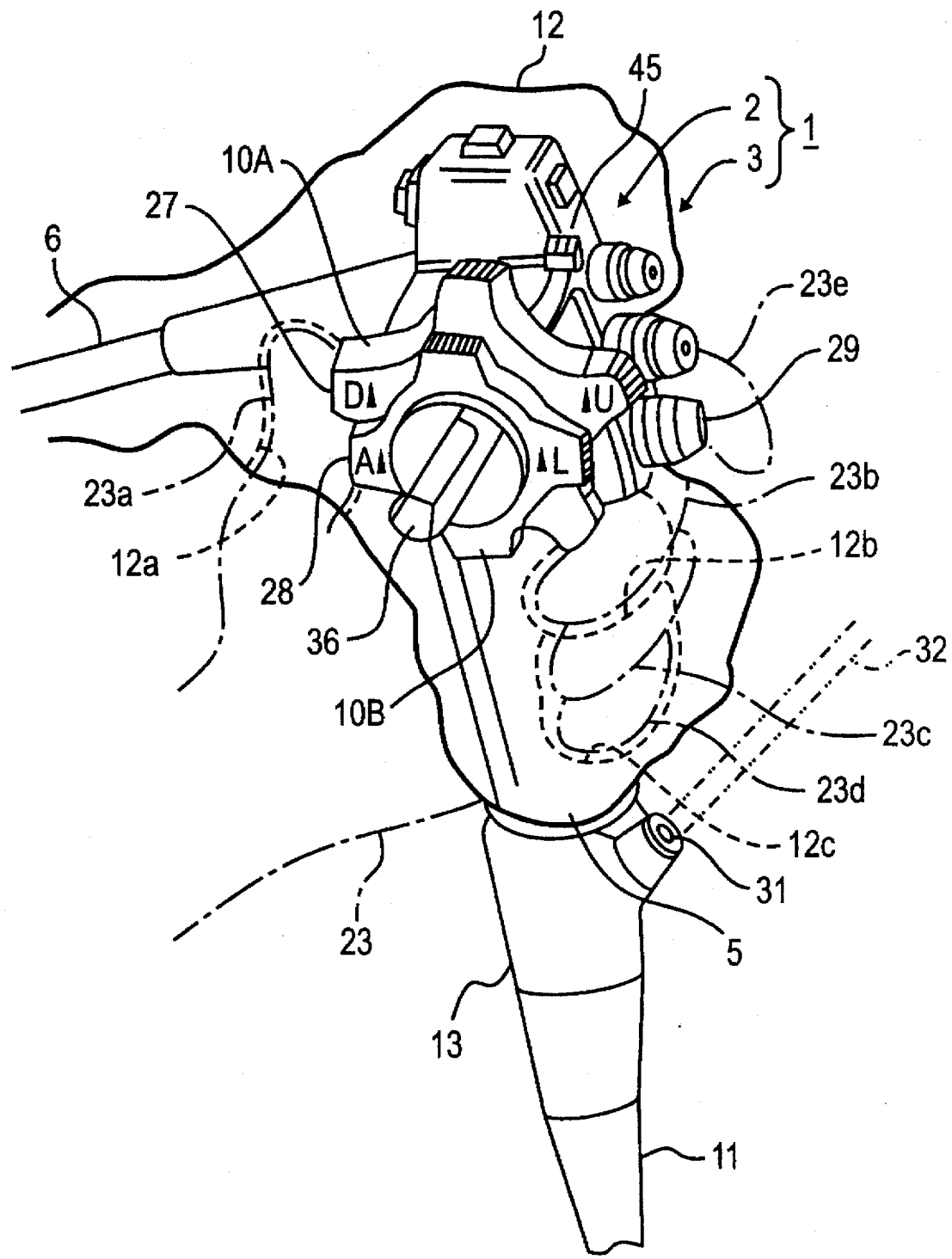
FIG. 3 is an illustration which shows the operator operating an operating member inside an operating portion cover from the outside of the operating portion cover in the first embodiment of this invention.

Referring to the drawings, embodiments of this invention will now be described specifically. FIGS. 1 to 3 relate to a first embodiment of this invention, and FIG. 1 shows schematically a structure of a cover-sheathed endoscope of the first embodiment, FIG. 2 shows the vicinity of a locking cap when an endoscope cover is attached to the endoscope, and FIG. 3 shows the state in which the operator operates an operating member inside an operating portion cover from the outside of the operating portion cover.

A cover-sheathed endoscope 1 of the first embodiment of this invention shown in FIG. 1 comprises an endoscope 2 and an endoscope cover 3 to cover the endoscope 2.

The endoscope 2 has an elongated inserting portion 4, a thick operating portion 5 formed at the back end of the inserting portion 4, and a universal cord 6 which extends outward from the operating portion 5. At the distal end of the universal cord 6 there is provided a connector (not shown), which can be connected to a light source device for providing light to a lightguide (not shown) in the endoscope 2, and a videoprocessor for signal processing for an imaging means (not shown) in the endoscope 2 (where the endoscope 2 is an electronic endoscope).

The inserting portion 4 comprises a rigid distal end portion 7, a bendable bending portion 8 formed at the back end of the distal end portion 7, and a long flexible portion 9 which extends from the back end of the bending portion 8 to the vicinity of the front end of the operating portion 5. The bending portion 8 can be bent up and down and left and right to be in an arbitrary direction by rotating an up-and-down bending knob 10A and a left-and-right bending knob 10B (see FIG. 3) arranged on the operating portion 5.

On the other hand, the endoscope cover 3 comprises an inserting portion cover 11 for covering the inserting portion 4 of the endoscope 2, and an operating portion cover 12 for covering mainly the operating portion 5. Between the inserting portion cover 11 and the operating portion cover 12, a locking cap 13 to be secured to the operating portion is arranged.

A distal end cover 14 is arranged at the distal end of the inserting portion cover 11 and provided with a transparent lens cover 15 for transmitting the illuminating light from the endoscope 2 and for obtaining an image to be observed. When the endoscope cover 3 is attached to the endoscope 2, a part of the distal end cover 14 is positioned with respect to and secured to a part of the distal end portion 7, and a part of the locking cap 13 is positioned with respect to and secured to a part of the operating portion 5. The back portion of the operating portion cover 12 covers a part of the universal cord 6 which extends from the operating portion 5.

By covering the endoscope 2 with the endoscope cover 3, the endoscope 2 becomes almost isolated from the outer environment. After the observation is done in this isolated state, the used endoscope cover 3 is discarded and exchanged for a new disinfected endoscope cover 3, so that the time and labor for washing and disinfecting the endoscope 2 can be saved.

A feature of this embodiment is that the operating portion cover 12 is made large enough in relation to the outside size of the operating portion 5 for easy attachment (there is enough clearance), and is provided in a predetermined part with finger putting portions 12a, 12b, and 12c into which an operator fits his or her fingers, the finger putting portions 12a, 12b, and 12c being protruded towards the inside of the operating portion cover 12 (inwardly towards the operating portion 5 which is to be covered by the operating portion cover 12).

These finger putting portions 12a, 12b, and 12c are arranged in appropriate positions for manipulating operating members, such as the up-and-down bending knob 10A and the left-and-right bending knob 10B, of the operating portion 5 which are moved and operated with the operating portion 5 covered with the operating portion cover 12. The finger putting portions 12a, 12b, and 12c are freely movable so that the operator can smoothly move his or her fingers fitted into the finger putting portions 12a, 12b, and 12c, to make rotational operation or the like of the operating members within the operating portion cover 12, such as the up-and-down bending knob 10A and the left-and-right bending knob 10B.

The finger putting portion 12a is on the opposite side from the two finger putting portions 12b and 12c with respect to the operating portion 5. The operating portion cover 12 is transparent, and with the operating portion 5 covered by the operating portion cover 12, the operator can visually recognize the operating members, such as the up-and-down bending knob 10A and the left-and-right bending knob 10B, of the operating portion 5 which are to be operated.

The material of the operating portion cover 12 may be a resin such as vinyl chloride or polyethylene which has a relatively low extensibility and is transparent or semi-transparent (as a result, the movement of the fingers can be seen), or a rubber resin which has a high extensibility.

FIG. 2 shows the vicinity of the locking cap 13 when the endoscope cover 3 (particularly the inserting portion cover 11) is attached to the endoscope 2.

The locking cap 13 comprises a gripping portion 16 to which the proximal end (back end) of the inserting portion cover 11 is secured and which is to be gripped by the operator, and a fixed portion to which the front end of the operating portion cover 12 is secured.

The fixed portion 17 is provided with a key 18, and the gripping portion 16 is provided with a key groove 19. The gripping portion 16 is axially slidable with respect to the fixed portion 17 as far as the key 18 is within the key groove 19. The fixed portion 17 is provided with a pawl 20, and the operating portion 5 is provided with a projection 21 having an outside diameter which is slightly larger than the inside diameter of the pawl 20.

When the cover is attached, the operating portion cover 12 is first turned inside out toward the inserting portion. Therefore, the finger putting portions 12a, 12b, and 12c directed towards the inside of the operating portion cover 12 in FIG. 1 is directed towards its outside this time (FIG. 2) because the cover is turned inside out. The finger putting portions 12a, 12b and 12c are inseparably integrated with the operating body portion cover, as shown in FIGS. 1 and 2. The locking cap 13 and the operating portion 5 (in the vicinity of the projection 21) are provided with a mark 22a and a mark 22b, respectively, for showing a UP direction (not necessarily UP) so as not to mistake the direction when attaching the cover. The marks 22a and 22b need not necessarily be recesses as in FIG. 2 and may be points or lines of a distinctive color.

Although the inserting portion cover 11 and the operating portion cover 12 may be separately made, the covers have to be connected together finally. In order to prevent the sealing characteristic of the connecting portion from being diverse from one worker to another, or to save time for the connecting operations, the covers are integrated via the locking cap 13 in this embodiment. As a result, if the inserting portion cover 11 is attached, the position matching of the operating portion cover 12 in the rotational and axial directions becomes unnecessary.

FIG. 3 shows the state in which the operator operates the operating portion 5 inside the operating portion cover 12 from the outside of the operating portion cover 12. As shown in FIG. 3, the up-and-down bending knob 10A as an operating member in the operating portion 5 is provided with, for example, five finger putting projections 27 having equal intervals between them, and the left-and-right bending knob 10B is provided with, for example, four finger putting projections 28 having equal intervals between them.

The projections 27 and the projections 28 are provided at their end surfaces with uneven portions for slip stopping. Also, the operating portion 5 is provided with a left-and-right bending brake 36 and an up-and-down bending brake lever 45 for braking the bending and for canceling this brake.

Next, the operation of this embodiment will be described.

When the endoscope cover 3 integrally formed by the inserting portion cover 11 and the operating portion cover 12 is attached to the endoscope 2, and especially when the inserting portion 4 is inserted into the inserting portion cover 11, the operating portion cover 12 is turned over to the side of the inserting portion cover 11 as shown in FIG. 2, so that the operating portion cover 12 does not disturb the insertion.

In FIG. 2, the inserting portion cover 11 is pulled up (as indicated by→A) by holding the gripping portion 16 of the locking cap 13 through the operating portion cover 12. When the pawl 20 has got over projection 21, the pawl 20 is engaged with the projection 21 and the inserting portion cover 11 is fixed to the endoscope 2. Then the operating portion cover 12 is turned back over (as indicated by→B) to be in the state as shown in FIG. 1.

As shown in FIG. 2, the gripping portion 16 can move in its axial direction (without rotation) as far as the key 18 can move in the key groove 19. Thus, even if, for example, a part of the inserting portion 4 is looped, the gripping portion 16 moves accordingly without too much load being applied to the inserting portion cover 11. Also, as the operating portion cover 12 is secured to the fixed portion 17, the operating portion cover 12 does not move although the gripping portion 16 moves. Thus, the finger putting portions 12a, 12b, and 12c are positioned properly with respect to the operating portion 5.

As shown in FIG. 3, among the fingers of the left hand 23 of the operator, a part of the thumb 23a is fitted to the finger putting portion 12a, a part of the middle finger 23b is fitted to the finger putting portion 12b, and parts of the third finger 23c and the little finger 23d are fitted to the finger putting portion 12c. The finger putting portions 12a, 12b, and 12c can be moved together with the fitted fingers.

The operating portion cover 12 is formed large enough with respect to the operating portion 5, and the operator can operate the finger putting projections 27 of the up-and-down bending knob 10A and/or the finger putting projections 28 of the left-and-right bending knob 10B with the thumb 23a and the middle finger 23b via the finger putting portions 12a and 12b as if there were no cover.

In the case of an endoscope having a treating instrument upheaving knob which is not shown, the upheaving knob can also be operated via the finger putting portion 12a. The positions of the finger putting portions 12a and 12b in the operating portion cover 12 influence the efficiency of the operation. Thus, in each cover, they are provided at predetermined positions which are considered to be the most appropriate.

The position of the finger putting portion 12a in the operating portion cover 12 will be described with reference to FIG. 3. For an operator who grips the operating portion 5 regardless of the position of the universal cord 6 as shown in FIG. 3, the root of the finger putting portion 12a is preferably positioned near the rotation axis of the bending knobs 10A and 10B when the cover is attached, if the position is represented in the axial direction (front-to-rear direction) of the endoscope.

On the other hand, for an operator who grips the operating portion 5 with the connecting portion of the universal cord 6 lying between the thumb 23a and the forefinger 23e, the root of the finger putting portion 12a is preferably positioned slightly behind the connecting portion of the universal cord 6.

The form of the finger putting portions 12a, 12b, and 12c may be such that they fit the fingers as shown in FIG. 3. However, they may also be in substantially tapered forms in which the thickness of the finger putting portions 12a, 12b, and 12c is larger than the normal finger size in their root parts and gradually gets closer to the normal finger size as the distance from their root parts increases.

If the operating portion cover 12 is shaped with a little clearance with respect to the operating portion 5 up to below the bending knobs 10A and 10B and the clearance suddenly becomes larger from below the bending knobs 10A and 10B, the finger putting portions 12b and 12c (or 12c) are not necessary.

If the finger putting portion 12b does not move independently it can be combined with the finger putting portion 12c. Contrarily, if the third finger and the little finger move independently, the finger putting portion 12c can be provided separately for the respective fingers. When the finger putting portions 12a, 12b, and 12c are made of a resin which does not expand very much, if they are made to fit large sized fingers, every operator will be able to use it.

The finger putting portions 12a, 12b, and 12c can be positioned in place by fixing the fixed portion 17 of the locking cap 13 (to which the operating portion cover 12 is secured) to the operating portion 5 as described above or by securing a control button 29 to the operating portion 5 from over the operating portion cover 12.

As the operating portion cover 12, a substantially linear and cylindrical cover may be attached by bending it from the operating portion 5 to the universal cord 6. However, if the cover is substantially L-shaped as shown in FIG. 1, its bending portion can serve as a means for positioning the finger putting portions 12a, 12b, and 12c in place.

Also, the operating portion cover 12 may be provided with a mark for positioning the finger putting portions 12a, 12b, and 12c in place when the cover is attached, and for confirming that they are positioned in place after the cover is attached. This applies to both the case in which the operating portion cover 12 is integrated with the inserting portion cover 11 and the case in which the operating portion cover 12 is separated from the inserting portion cover 11.

If a part of the operating portion cover 12 other than the finger putting portions 12a, 12b, and 12c coils around the up-and-down bending knob 10A or the left-and-right bending knob 10B when they are rotated and operated, the efficiency of operation will decline. Therefore, it is preferable that enough clearance be kept between the up-and-down and left-and-right bending knobs 10A and 10B (a treating instrument upheaving knob, if any) and the operating portion cover 12.

If the operating portion 5 is gripped as if being wrapped up from the outside of the operating portion cover 12 by the third finger 23c and the little finger 23d which do not operate the up-and-down bending knob 10A and the left-and-right bending knob 10B, the clearance between the up-and-down and left-and-right bending knobs 10A and 10B and the operating portion cover 12 is likely to become narrow.

Thus, the operating portion cover 12 is provided with the finger putting portion 12c, via which the operating portion 5 can be gripped with the bulge (clearance) of the operating portion cover 12 maintained in the vicinity of the operating portion 5.

Further, although it is not shown, the inserting portion cover 11 is provided with channels for feeding air and water and for suction which have openings in the distal end cover 15. These channels are coupled to a fluid control device of an electromagnetic valve control type (an outside device separate from the endoscope) which is not shown. In order to control the feeding of air and water and the suction by the electromagnetic valve, the operating portion 5 is provided from the outside of the operating portion cover 12 with the control button 29 which is a member different from the operating portion 5, as shown in FIG. 3.

In this way, because the first finger 23e can operate the button 29 without the cover, an operation error can be prevented. However, in some cases, in order to make the construction simple, the control button 29 may be provided in the operating portion 5 and operated via the operating cover portion 12.

Also, a part of the suction channel (not shown) provided in the inserting portion cover 11 has a treating instrument inserting inlet 31 in a part of the locking cap 13 in order to insert the treating instrument therethrough. Here, in order that the bulge of the operating portion cover 12 should not hinder the insertion of the treating instrument, the operating portion cover 12 is formed so as not to intersect the extension line 32 of the treating instrument inserting inlet 31.

If the finger putting portions 12a, 12b, and 12c are made of the same material as and formed integrally with the operating portion cover 12, production costs can be reduced.

However, as the finger putting portions, 12a, 12b, and 12c, finger stalls made separately may be connected to the operating portion cover 12. Generally, an operator wears a rubber glove on the left hand 23. If the operating portion cover 12 is made of an inexpensive material such as vinyl and the finger putting portions 12a, 12b, and 12c are made of a rubber resin, the finger putting portions 12a, 12b, and 12c will have more affinity for the rubber glove of the left hand 23, so that a good feeling of operation will be achieved as if the operating portion cover 12 did not exist.

Further, if the finger putting portions 12a, 12b, and 12c are made of a rubber resin, and are formed, for example, in an ordinary finger size, a person with large fingers can put his or her fingers to the finger putting portions by slightly spreading them, and the one size of finger putting portions is enough for every operator to make operation with a good feeling. Also, in addition to a rubber resin, any material such as cloth or a porous resin elastic may be used.

According to the first embodiment, because the finger putting portions 12a, 12b, and 12c are provided, the bending knobs 10A and 10B to be extensively largely rotated and operated can be well operated even from over the operating portion cover 12 wrapping the operating portion 5 wholly.

Moreover, various sizes may be prepared for the finger putting portions 12a, 12b, and 12c whether they are made integrally with or separately from the operating portion cover 12. In this way the operator can choose a size fitting to his or her fingers to make a better operation.

Figure 4:
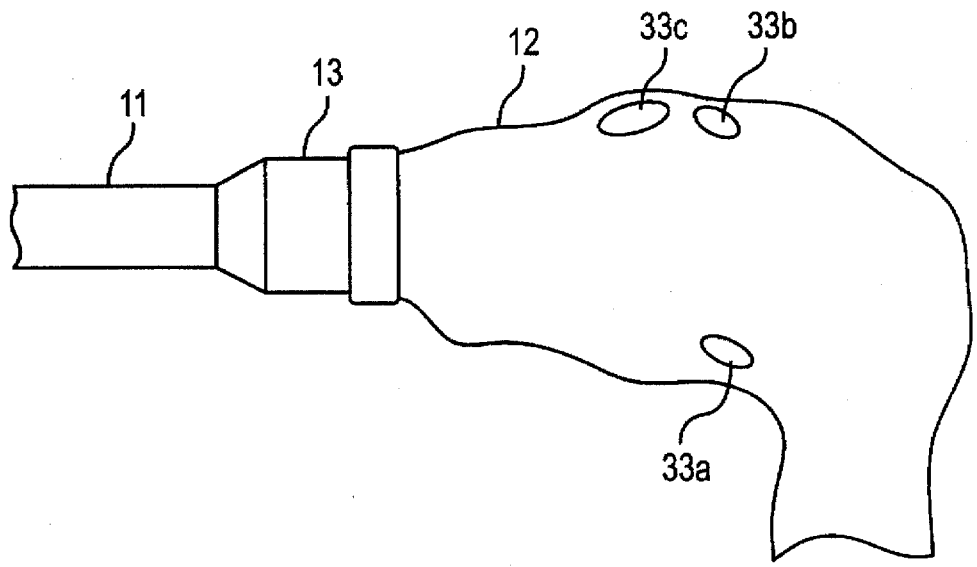
FIG. 4 is a side view of the vicinity of an operating portion cover of a second embodiment of this invention.

Next, referring to FIG. 4, a second embodiment of this invention will be described.

This embodiment relates to a variation of the finger putting portions of the first embodiment. As shown in FIG. 4, in this embodiment finger putting openings 33a, 33b, and 33c are provided instead of the finger putting portions 12a, 12b, and 12c of the first embodiment. Although in FIG. 4 these finger putting openings 33a, 33b, and 33c are in the form of bores, they may be slits having circumferences of the same length.

Next, the operation of this embodiment will be described. As in FIG. 3 of the first embodiment, the thumb 23a of the left hand 23 of the operator wearing a rubber glove is inserted into the finger putting opening 33a, the middle finger 23b is inserted into the finger putting opening 33b, and the third finger 23c and the little finger 23d are inserted into the finger putting opening 33c.

In this way, with the rubber glove, a cover in the same form as in FIG. 3 can be realized. The effect of this embodiment is as follows.

As the operator can operate the operating members such as the bending operating knobs 10A and 10B directly with the fingers, the feeling of operation will be even better than that in the first embodiment.

Figure 5:
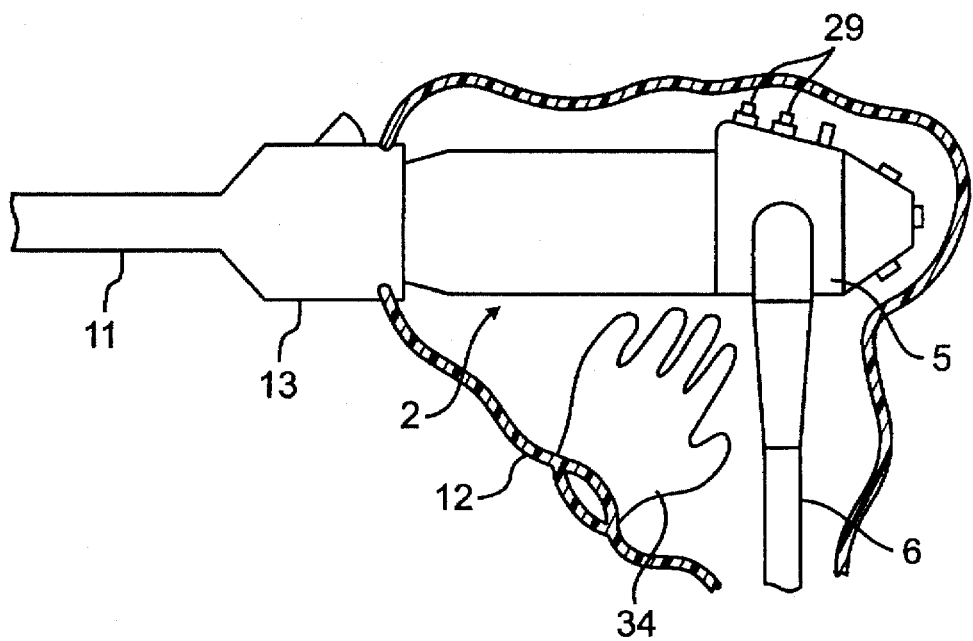
FIG. 5 is a side view of the vicinity of an operating portion cover of a third embodiment of this invention.

Next, referring to FIG. 5, a third embodiment of this invention will be described. In this embodiment, an operating portion cover 12 is provided (at its predetermined position) with a glove portion 34 (the finger parts of the glove portion 34 being finger putting portions) instead of the finger putting portions 12a, 12b, and 12c of the first embodiment.

The glove portion 34 may be formed integrally with the operating portion cover 12, or a separate glove may be provided to the operating portion cover 12. When the glove is a separate portion, the operating portion cover 12 may be made of, for example, an inexpensive transparent vinyl resin, and the glove portion 34 may be made of, for example, a rubber resin.

Next, the operation will be described. The left hand of the operator is inserted into the glove portion 34 to operate operating members of an operating portion 5. The operator need not wear a rubber glove on the left hand. Even if a glove is not worn, and if the glove portion 34 is made of a rubber resin, the operating members can be operated as if the endoscope had no cover on it.

According to this third embodiment, compared with the first embodiment, as the glove portion 34 covers not only parts of the fingers of the operator but also covers up to the wrist, the fingers of the operator will not slip off the finger putting portions during the operation and good operation can be maintained.

Next, referring to FIG. 6, a fourth embodiment of this invention will be described. In this embodiment, operating members of an operating portion 5 can be operated by the right hand via an operating portion cover 12 which is similar to those referred to in the first, second, and third embodiments.

Figure 6:
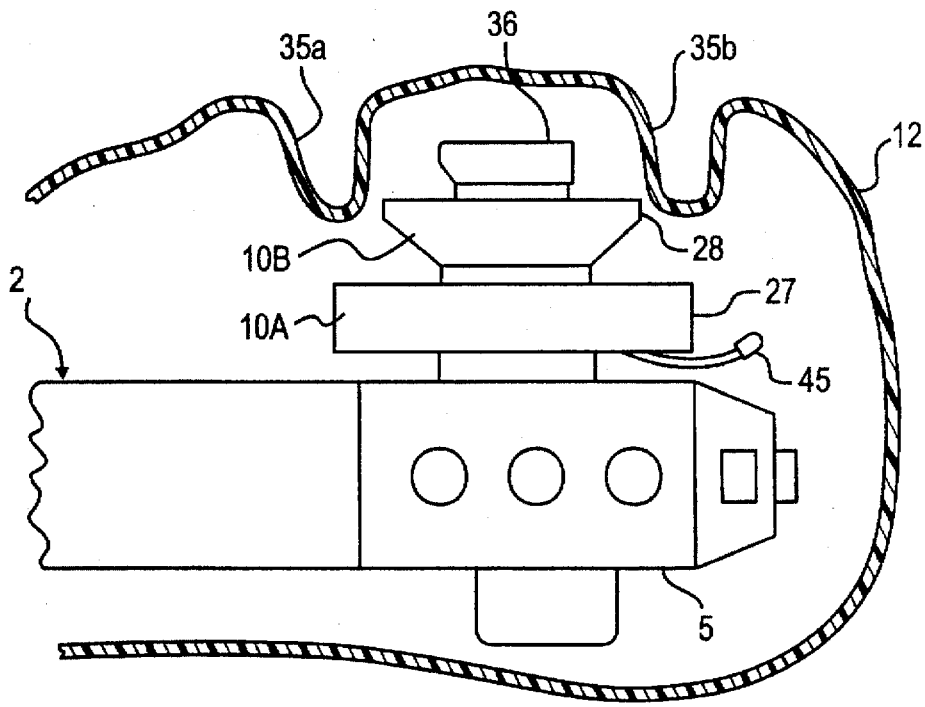
FIG. 6 is a side view of the vicinity of an operating portion cover of a fourth embodiment of this invention.

Although not shown in FIG. 6, the operating portion cover 12 is provided with the finger putting portions 12a, 12b, and 12c where fingers of the left hand 23 fit, or the finger putting openings 33a, 33b, and 33c, or the glove portion 34, which are described in the first, second, and third embodiments. In addition, there are provided finger putting portions 35a and 35b where fingers of the right hand of the operator can be fitted.

These finger putting portions 35a and 35b may be separately formed such that the respective fingers can be put into these portions 35a and 35b, or may be integrated into a ring-shaped recess.

Although in FIG. 6 the finger putting portions 35a and 35b are formed integrally with the operating portion cover, they may be formed as finger stalls made separately from the operating portion cover 12, or they may be openings for the right hand or a glove portion for the right hand as in the second and third embodiments.

Next, the operation will be described. Although an up-and-down bending knob 10A and a left-and-right bending knob 10B of the operating portion 5 can be operated only with the left hand, especially the left-and-right bending knob 10B is easier to be operated with the right hand.

If one or a plurality of fingers of the right hand are put into the finger putting portions 35a and 35b to operate the left-and-right bending knob 10B, the surrounding operating portion cover 12 will not coil around the left-and-right bending knob 10B and the left-and-right bending brake lever 36 which brakes the rotation of the left-and-right bending knob 10B and cancels the brake, so that successful operation with the right hand can be done.

As stated above, the fourth embodiment improves the efficiency of operation with the right hand of the left-and-right bending knob 10B and the left-and-right bending brake lever 36.

Next, referring to FIG. 7, a fifth embodiment of this invention will be described. Similar to the fourth embodiment, this embodiment is an example of improving the efficiency of operation with the right hand via an operating portion cover 12.

Figure 7:
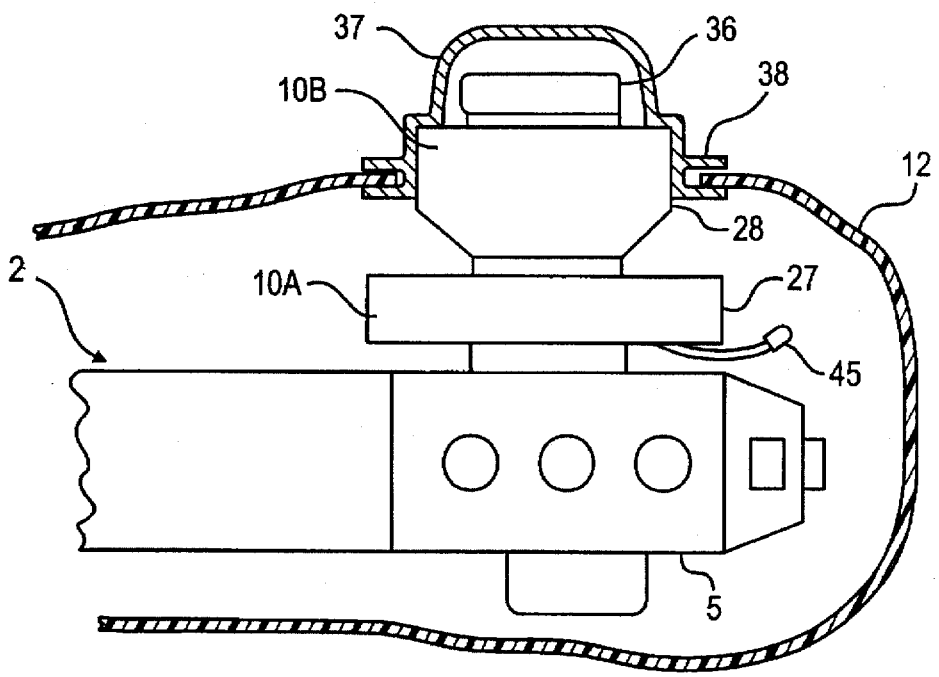
FIG. 7 is a cross-sectional view of the vicinity of an operating portion cover of a fifth embodiment of this invention.

As shown in FIG. 7, the operating portion cover 12 is provided with a rotating cover portion 37 rotatable with respect to the operating portion cover 12.

The width(height) of a left-and-right bending knob 10B is thicker than a usual one, and a part of the rotating cover portion 37 can be removably attached to a part of the left-and-right bending knob 10B. FIG. 7 shows the state in which the rotating cover portion 37 is fitted to a part of the left-and-right bending knob 10B.

Although the outside form of the fitting part of the rotating cover portion 37 is not shown, it takes the shape of the left-and-right bending knob 10B of FIG. 3. However, a flange portion 38 is circular. The rotating cover portion 37 may preferably be made of a rubber resin. The rotating cover portion 37 is fitted to a part of the left-and-right bending knob 10B, but it does not touch the left-and-right bending brake lever 36.

Next, the operation will be described. Also in this embodiment, an up-and-down bending knob 10A and the left-and-right bending knob 10B can be operated only by the left hand (although the finger putting portions for the left hand are not shown, they are of one of the types described in the first to third embodiments). When the left-and-right bending knob 10B is operated by the left hand, the portion where the rotating cover portion 37 is not fitted can be operated.

When the left-and-right bending knob 10B is operated by the right hand, the operation can be made by holding the portion to which the rotating cover portion 37 is fitted, or by touching it by fingers.

As the rotating cover portion 37 is rotatable with respect to the operating portion cover 12, the operating portion cover 12 will not be twisted even if the left-and-right bending knob 10B is rotated via the rotating cover portion 37 by, for example, about 180° at a stretch.

Further, as the outside form of the fitting portion between the rotating cover portion 37 and the left-and-right bending knob 10B takes the shape of the left-and-right bending knob 10B (see the outside form of the left-and-right bending knob 10B of FIG. 3), the left-and-right bending knob 10B stands out against the operating portion cover 12, so that operation can be made more easily (especially when holding the knob).

Because the left-and-right bending knob 10B stands out, its position and rotation angle are recognizable even when the operating portion cover 12 is black in order to conceal stains, or white to show stains on the contrary, or in any other colors other than transparent.

If the rotating cover portion 37 is made of a rubber resin, a left-and-right bending brake lever can be rotatively operated (the rotation angle being 90° or more) via the upper part of the rotating cover portion 37 with the left-and-right bending knob 10B being stopped by, for example, fingers of the left hand. At this time, a part of the rotating cover portion 37 is stretched.

According to this embodiment, when operating the left-and-right bending knob 10B with the right hand, it can be largely rotated at one time in comparison with the fourth embodiment.

Figure 8:
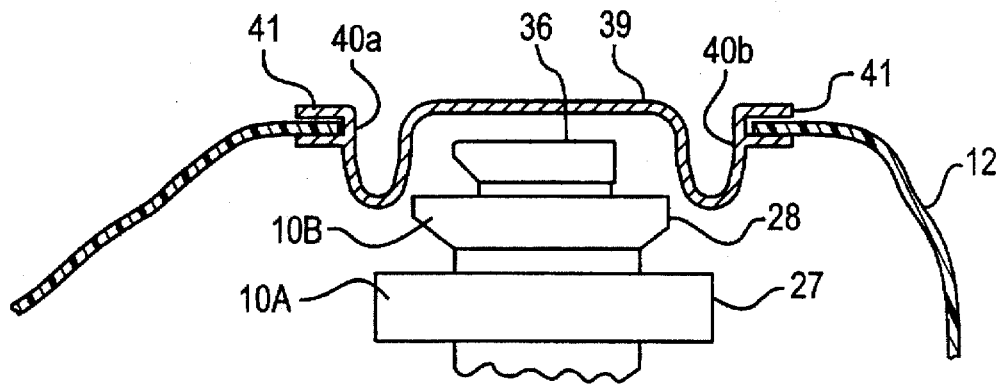
FIG. 8 is a cross-sectional view of the vicinity of a rotating cover portion of a sixth embodiment of this invention.

Next, referring to FIG. 8, a sixth embodiment of this invention will be described. The structure of this embodiment is a variation of the fourth and fifth embodiments. As shown in FIG. 8, an operating portion cover 12 is provided with a rotating cover portion 39 for the right hand operation.

The rotating cover portion 39 is provided with a plurality of finger putting portions 40a and 40b. These finger putting portions 40a and 40b may be separate such that the respective fingers can be put into the portions, or may be integrated into a ring-shaped groove so that a plurality of fingers can be easily put in it. Although the rotating cover portion 39 may preferably be formed of a rubber resin, it may be formed of any other resins which are relatively flexible. Also, it may be formed of paper which is not readily torn.

If a left-and-right bending brake lever 36 is low, or it is embedded in a left-and-right bending knob 10B, the rotating cover portion 39 may be flat without having the finger putting portions 40a and 40b.

Next, the operation will be described. It is similar to the operation of the fourth embodiment. What is different is that the finger putting portions 40a and 40b for the right hand (as the rotating cover portion 39) are rotatable with respect to the operating portion cover 12.

Thus, a rotating operation larger than that of the fourth embodiment can be done at a time. During the rotative operation the rotating cover portion 39 will not come off the operating portion cover 12 because of the operation of the flange 41.

According to the sixth embodiment, in addition to the effects of the fifth embodiment, the structure is simpler than in the fifth embodiment and it is not necessary to fit the rotating cover portion 39 to the left-and-right bending knob 10B.

Next, referring to FIG. 9, a seventh embodiment of this invention will be described. A knob cover portion 42 is provided at a predetermined position of an operating portion cover 12.

Figure 9:
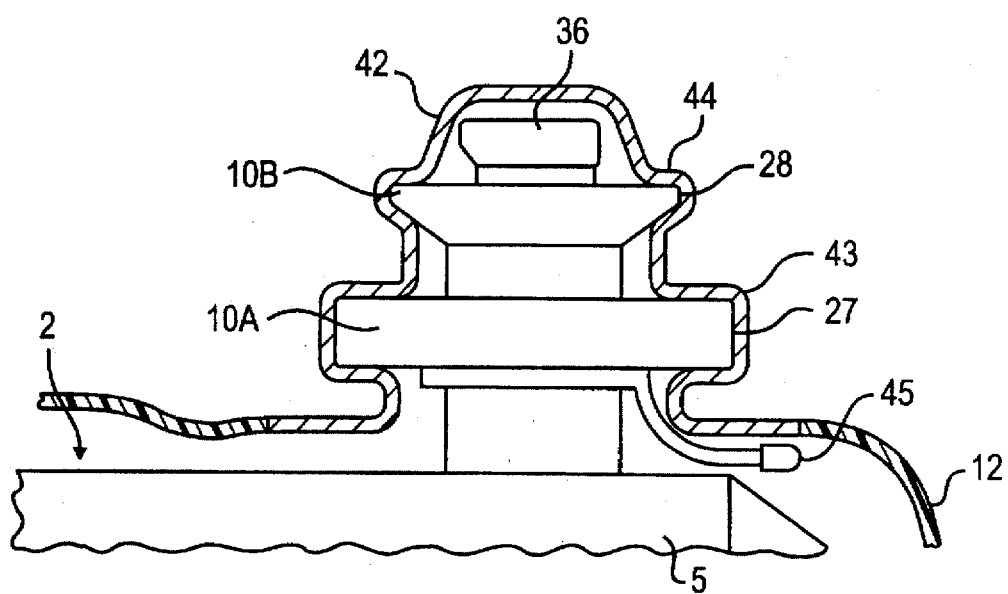
FIG. 9 is a cross-sectional view of the vicinity of a rotating cover portion of a seventh embodiment of this invention.

As shown in FIG. 9, the knob cover portion 42 is formed so that it will fit to an up-and-down bending knob 10A and a left-and-right bending knob 10B (finger putting portions 43 and 44). Namely, if the external forms of the up-and-down bending knob 10A and the left-and-right bending knob 10B are such as shown in FIG. 3, the finger putting portions 43 are five projecting portions to which finger putting projections 27 can fit, and the finger putting portions 44 are four projecting portions to which finger putting projections 28 can fit (the knob cover portion 42 is a single member having such a form).

The knob cover portion 42 may preferably be formed of a rubber resin and may be attached to the operating portion cover 12 formed of a vinyl resin, or the operating portion cover 12 may be also formed of a rubber resin and integrated with the knob cover portion 42.

Next, the operation is described. When an operating portion 5 is covered by the operating portion cover 12, the knob cover portion 42 is mounted such that the finger putting portions 43 fit to the finger putting projections 27 and the finger putting portions 44 fit to the finger putting projections 28. Since the left-and-right bending knob 10B is smaller than the up-and-down bending knob 10A, the knob cover portion 42 can be easily mounted.

The operator operates the up-and-down bending knob 10A and the left-and-right bending knob 10B by putting the fingers of either the left hand or the right hand to the finger putting portions 43 and the finger putting portions 44. If the knob cover portion 42 is made of a rubber resin, the up-and-down bending knob 10A and the left-and-right bending knob 10B can be rotatively operated with the knob cover portion 42 between the finger putting portions 43 and the finger putting portions 44, and under the finger putting portions 43 being stretched.

A left-and-right bending brake lever 36 can be rotatively operated via the cover portion over it (there is enough clearance) without rotating the finger putting portions 44, by stretching the cover portion in the vicinity of the left-and-right bending brake lever 36. Also, an up-and-down bending brake lever 45 can be rotatively operated (the rotation angle is 45° or less) via a part of the knob cover portion 42 or a part of the operating portion cover 12.

The clearance between the operating portion cover 12 and the operating portion 5 is smaller than that in the foregoing embodiments. Therefore, even when the operating portion cover 12 is attached to the operating portion 5, the operating portion 5 appears almost as if the cover were not attached. Accordingly, the operating portion 5 can be undisturbedly operated.

Figure 10:
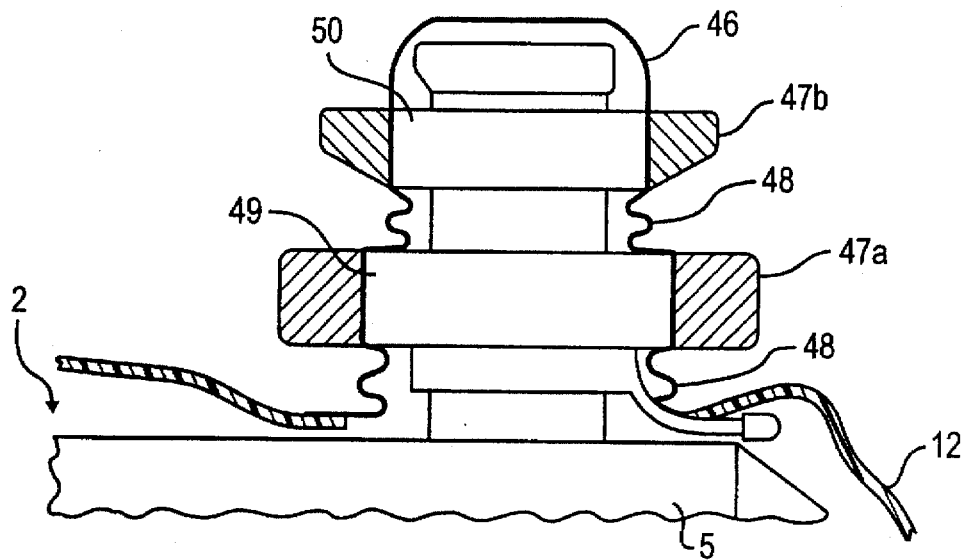
FIG. 10 is a cross-sectional view of the vicinity of a knob cover portion of an eighth embodiment of this invention.

Next, referring to FIG. 10, an eighth embodiment of this invention will be described. A knob cover portion 46 is provided at a predetermined position of an operating portion cover 12 which is similar to that of the seventh embodiment. The knob cover portion 46 may preferably be made of a rubber resin, but may also be of other flexible resins.

The knob cover portion 46 is provided with finger putting portions 47a and 47b formed of a hard resin or the like which is different from the material of the knob cover portion 46.

Between the finger putting portions 47a and 47b, and beneath the finger putting portions 47a, the knob cover portion 46 has folded portions 48 formed as bellows. The numbers of the peaks and valleys of the folded portion 48 are arbitrary.

An up-and-down bending knob 49 and a left-and-right bending knob 50 provided to an operating portion 5 are substantially circular. The finger putting portions 47a and 47b can be coupled to the up-and-down bending knob 49 and the left-and-right bending knob 50, respectively via the knob cover portion 46 or with parts of the knobs 49 and 50 penetrating through the knob cover portion 46. After the coupling, the up-and-down bending knob 49 will move in response to the rotation of the finger putting portions 47a and the left-and-right bending knob 50 will move in response to the rotation of the finger putting portions 47b.

As the left-and-right bending knob 50 is smaller than the up-and-down bending knob 49, the coupling is easy.

The knob cover portion 46 and the operating portion cover 12 may be either different members or formed integrally.

Also, the knob cover portion 46 and the finger putting portions 47a and 47b may be integrally formed of a resin. In that case, the thick finger putting portions 47a and 47b are relatively rigid, whereas the thin knob cover portion 46 is relatively flexible.

When the finger putting portions 47a and 47b are coupled to the up-and-down bending knob 49 and the left-and-right bending knob 50, their outward appearance is, for example, similar to that of the up-and-down bending knob 10A and the left-and-right bending knob 10B in FIG. 3.

The operation of this embodiment is substantially the same as that of the seventh embodiment. What is different is that because the folded portions 48 formed in the knob cover portion 46 are stretchable, the up-and-down bending knob 49 and the left-and-right bending knob 50 can be rotated largely, without applying much force. Further, the operating portion 5 is isolated completely from the outside environment.

Moreover, because the finger putting portions 47a and 47b are rigid members, their outward appearance and the feeling of operation are closer to those of an ordinary, non-sheathed endoscope in comparison with the seventh embodiment.

The effects of this embodiment are as follows. In comparison with the seventh embodiment, even when the cover is attached, the outward appearance and the feeling of operation are closer to those of an ordinary, non-sheathed endoscope, and even if the knob is largely rotated, much force for rotation is not necessary.

Figure 11:
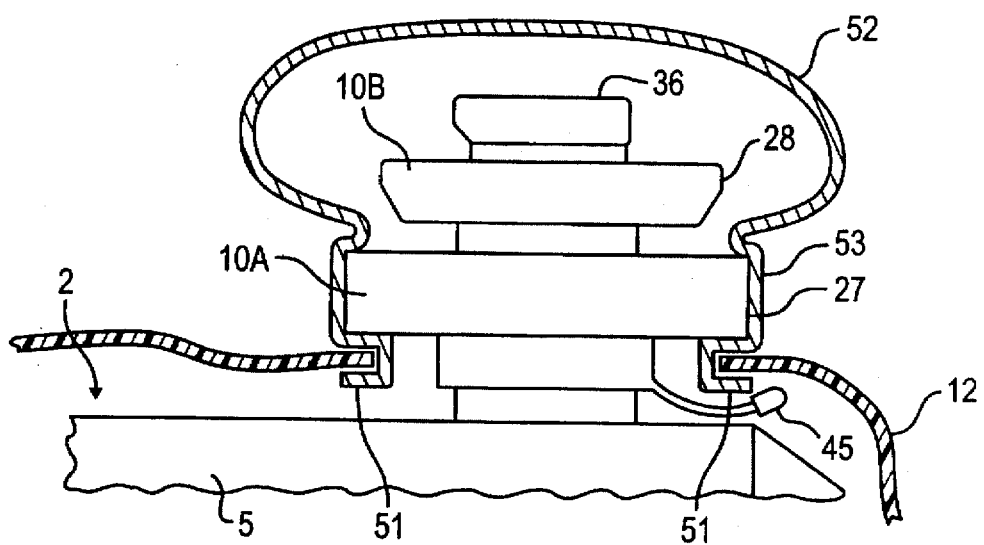
FIG. 11 is a cross-sectional view of the vicinity of a knob cover portion of a ninth embodiment of this invention.

Next, referring to FIG. 11, a ninth embodiment of this invention will be described. An operating portion cover 12 is provided at its predetermined position with a knob cover portion 52 which is rotatable with respect to the operating portion cover 12 owing to a flange portion 51.

The knob cover portion 52 has finger putting portions 53, and the finger putting portions 53 are projections to which finger putting projections 27 of an up-and-down bending knob 10A can be fitted.

The cover in the vicinity of a left-and-right bending knob 10B is formed large enough with respect to the left-and-right bending knob 10B (it is expanded beyond the outside diameter of the finger putting portions 53).

The material of the knob cover portion 52 may preferably be a rubber resin, but it may be another resin such as vinyl.

Next, the operation will be described. When the operating portion cover 12 is attached to an operating portion 5, the finger putting portions 53 of the knob cover portion 52 are fitted to the finger putting projections 27 of the up-and-down-bending knob 10A.

The attachment is easy because the left-and-right bending knob 10B is smaller than the up-and-down bending knob 10A.

The knob cover portion 52 is not coupled to the left-and-right bending knob 10B. The up-and-down bending knob 10A can be operated either by the fingers of the left hand or the right hand via the finger putting portions 53. The left-and-right bending knob 10B is operated via the expanded part of the knob cover 52. Because the knob cover portion 52 has enough clearance, the left-and-right bending knob 10B can be relatively largely rotated with respect to the up-and-down bending knob 10A with a part of the knob cover portion 52 being stretched and twisted.

This embodiment has the following effect. In comparison with the seventh and eighth embodiments, the time for attaching the cover can be saved because the knob cover portion 52 is not coupled to the left-and-right bending knob 10B.

Figure 12:
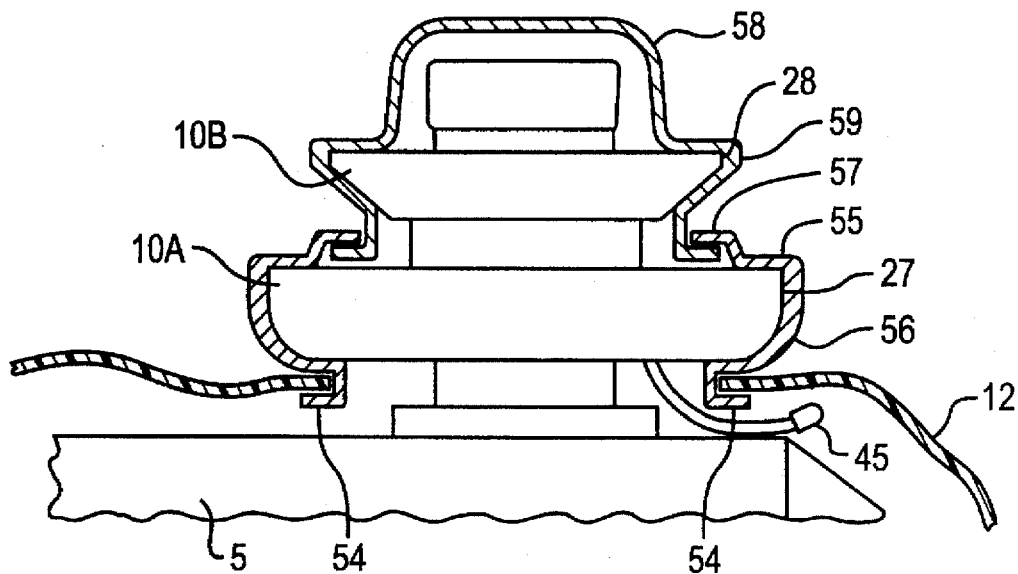
FIG. 12 is a cross-sectional view of the vicinity of a knob cover portion of a tenth embodiment of this invention.

Next, referring to FIGS. 12 and 13, a tenth embodiment of this invention will be described. A knob cover portion 55 rotatable owing to a circular flange portion 54 is provided at a predetermined position of an operating portion cover 12. The knob cover portion 55 is provided with finger putting portions 56 formed so as to fit to finger putting projections 27 of an up-and-down bending knob 10A (the knob cover portion 55 is mostly formed by the finger putting portions 56, the flange portion 54 and a circular flange portion 57).

The knob cover portion 55 is provided with a knob cover portion 58 rotatable owing to the circular flange portion 57. The knob cover portion 58 is provided with finger putting portions 59 formed so as to fit to finger putting projections 28 of a left-and-right bending knob 10B.

Figure 13:
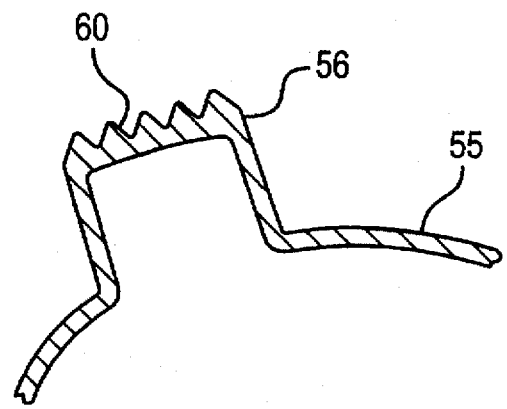
FIG. 13 is a cross-sectional view of a slip preventing portion provided to a finger putting portion of the knob cover portion of the tenth embodiment of this invention.

As shown in FIG. 13, the finger putting portion 56 of the knob cover portion 55 is provided on its peripheral end face with a slip preventing portion 60 formed by a plurality of fine notches. The same portion may be provided to the finger putting portion 59. The knob cover portions 55 and 58 may preferably be made of a rubber resin.

Next, the operation will be described. Although it is similar to that of the seventh embodiment, in this embodiment the amount of force for operating the knobs remains almost unchanged even when the knobs are largely rotated via the finger putting portions 56 and 59, because the knob cover portions 55 and 58 are rotatable with respect to the operating portion cover 12.

Further, also in this embodiment, it is easy to attach the knob cover 55 because the left-and-right bending knob 10B is smaller than the up-and-down bending knob 10A.

In addition, this embodiment has the effect that the operating fingers will not slip easily from the finger putting portions 56 (and 59) because of the slip preventing portions 60 on the finger putting portions 56 (and/59), and efficiency of operation will improve.

Next, referring to FIGS. 14 and 15, an eleventh embodiment of this invention will be described. A flange member 61 made of a rigid resin is fixed by gluing or heat welding to a predetermined position of an operating portion cover 12 made of a flexible resin, or cloth which does not let liquid through easily.

A knob cover portion 62 is rotatably provided to the flange member 61, and a knob cover portion 63 is rotatably provided to the knob cover portion 62. Finger putting portions 62a and 63a are provided to the knob cover portions 62 and 63, respectively. The knob cover portions 62 and 63 are made of a rigid resin.

The flange member 61 has a pawl 64a, the knob cover portion 62 has pawls 64b and 64c, and the knob cover portion 63 has a pawl 64d, and these pawls are to prevent the flange member 61 and the knob cover portions 62 and 63 from being separated. As shown in FIG. 14, the shapes of these pawls 64a, 64b, 64c and 64d are such that at the time of assembly the pawls 64b and 64d are strongly pushed down to engage with the pawls 64a and 64c, respectively and then will not be disengaged even if they are pulled.

On top of the knob cover portion 63, a cap-shaped cover portion 65 made of a flexible material such as a rubber resin is provided rotatably or fixedly with respect to the knob cover portion 63.

Although an up-and-down bending knob 66 and a left-and-right bending knob 67 are substantially circular, they have protruding portions or recess portions for coupling the knob cover portions 62 and 63 to the knobs.

A projection 68 is provided on the upper part of the left-and-right bending knob 67. Also, the lower part of the cap-shaped cover portion 65 is provided with a projection 69 having an inside diameter such that the projection 69 climbs over the projection 68 to fit to the knob 67 just under the projection 68 when the knob cover portion 63 is coupled to the left-and-right bending knob 67.

Figure 15:
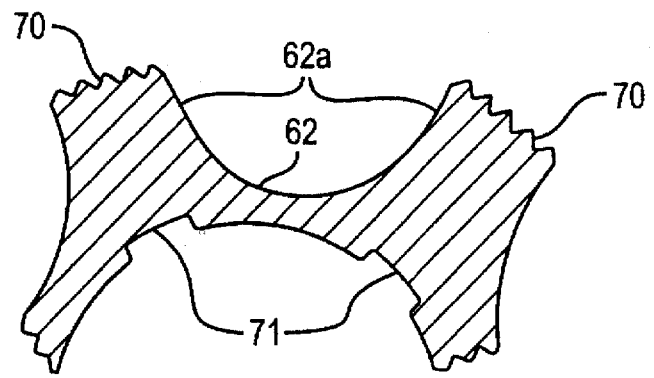
FIG. 15 is a cross-sectional view of a slip preventing portion provided to a finger putting portion of the knob cover portion of the eleventh embodiment of this invention.

Each of the finger putting portions 62a of the knob cover portion 62 is provided, where its outside diameter is largest, with a slip preventing portion 70 formed by a plurality of fine notches as shown in FIG. 15 (its operation and effect are the same as those of the preceding embodiment).

Of course, the slip preventing portion 70 may be provided to the finger putting portion 63a.

As shown in FIG. 15, the knob cover portion 62 is provided inside with a number of recesses 71 into which the up-and-down bending knob 66 can be fitted so as not to be rotated with respect to the knob cover portion 62, the number of recesses 71 corresponding to that of the finger putting portions 62a.

As such, the knob cover portion 62 can be coupled to the up-and-down bending knob 66 by rotating the knob cover portion 62 with respect to the up-and-down bending knob 66. The same applies to the left-and-right bending knob 67 and the knob cover portion 63.

In this embodiment as well as other embodiments described above, the positional relationship between the up-and-down bending knob 66 and the left-and-right bending knob 67 and between the knob cover portions 62 and 63 may be reversed.

Next, the operation will be described. Just like in the aforesaid embodiments, a part of the operating portion cover 12 is turned inside out as shown in FIG. 2 before it is attached to the operating portion 5. Also in this embodiment, a part of the operating portion cover 12 is turned over. The operating portion cover 12 may be turned over in front of the flange member 61 (i.e., on the left side of the drawing) together with the flange member 61, the knob cover portions 62 and 63, and the cap-shaped cover 65. Also, the operating portion cover 12 may be turned over behind the flange member 61 (i.e., on the right side of the drawing) to cover up the knob cover portions 62 and 63 and the cap-shaped cover 65.

In either case, because the flange portion 61, the knob cover portions 62 and 63, and the cap-shaped cover portion 65 are formed as a unit with respect to the operating portion cover 12, they do not come apart when the operating portion cover 12 is attached to and removed from the operating portion 5, and it can be handled well.

Figure 14:
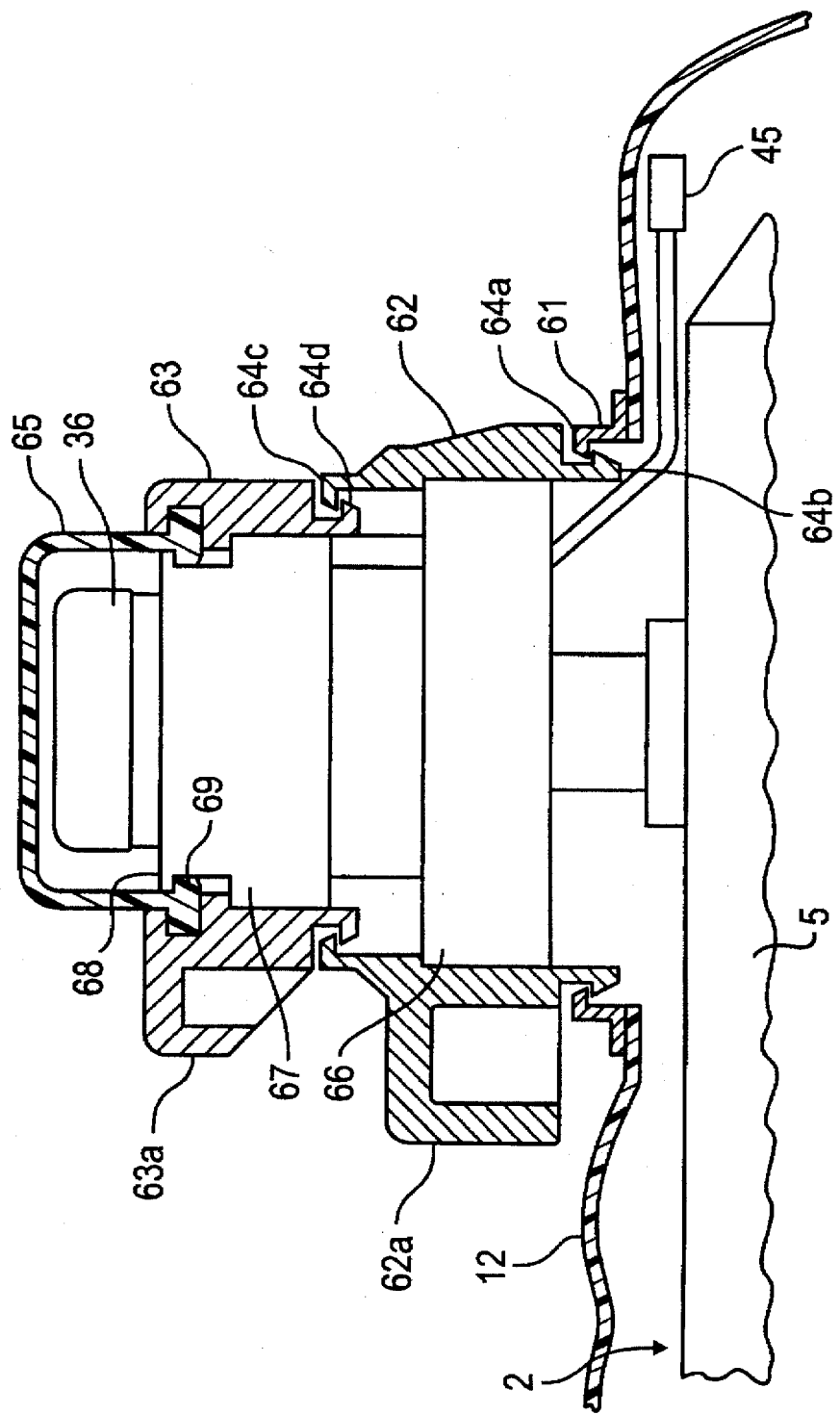
FIG. 14 is a cross-sectional view of the vicinity of a knob cover portion of an eleventh embodiment of this invention.

When (or after) the operating portion cover 12 is attached to the operating portion 5, the flange member 61 is located in the position shown in FIG. 14 after getting over a left-and-right bending brake lever 36, the left-and-right bending knob 67, and the up-and-down bending knob 66 in this order.

Therefore, a moderate amount of room (sag) is necessary for the operating portion cover in front of the flange member 61 (i.e., on the left side of the drawing). However, too much sag will disturb the operation or will affect the external form. Accordingly, in any operating portion cover, the position where the flange member 61 (and the knob cover portions 62 and 63, and the cap-shaped cover portion 65) are attached to the operating portion cover 12 always have to be the most appropriate predetermined position.

When the knob cover portion 62 is coupled to the up-and-down bending knob 66 and the knob cover portion 63 is coupled to the left-and-right bending knob 67, thereby attaching the operating portion cover 12 to the operating portion 5, it is difficult for the knob cover portions 62 and 63 to come off from the up-and-down bending knob 66 and the left-and-right bending knob 67, respectively. However, the knob cover portions 62 and 63 may be unstable.

Therefore, the projection 69 made of a rubber resin or the like climbs over the projection portion 68 at the upper part of the left-and-right bending knob 67 to prevent the unstableness. Further, the knob cover portions 62 and 63 can be coupled easily because the left-and-right bending knob 67 is smaller than the up-and-down bending knob 66 and the left-and-right bending brake lever 36 is smaller than the left-and-right bending knob 67.

The up-and-down bending knob 66 and the left-and-right bending knob 67 are operated via the finger putting portions 62a and 63a, respectively. The left-and-right brake lever 36 is operated via the cap-shaped cover portion 65, and an up-and-down brake lever 45 is operated via a part of the operating portion cover 12. Since the finger putting portions 62a and 63a are rigid and their forms are the same as those of a conventional endoscope, their feeling of operation is the same as that of a conventional endoscope.

This embodiment has the following effects. In comparison with the tenth embodiment, the knob cover portions can be easily coupled to and removed from the knobs by simply moving them in the axial direction of the knobs, and the feeling of operation can be the same as that of a conventional endoscope because the finger putting portions are rigid.

Next, referring to FIG. 16, a twelfth embodiment of this invention will be described. In this embodiment, a treating instrument upheaving device (not shown) is provided at the distal end of an inserting portion cover (not shown) or at the distal end of an endoscope 2, and an operating portion 5 of the endoscope 2 is provided with an upheaving operation knob 72.

The upheaving operation knob 72 is rotatably provided coaxially with a rotation axis 73 of a bending operation knob (not shown) which is provided on the upheaving operation knob 72, namely closer to the reader than the upheaving operation knob 72. However, the axis of the upheaving operation knob 72 may be different from the rotation axis of the bending operation knob.

A finger putting portion 74 is provided to an operating portion cover 12. The finger putting portion 74 has a slip preventing portion 75 formed by notches. The finger putting portion 74 may preferably be a resin or a metal. However, it may also be a rubber resin. In that case, the operating portion cover 12 may also be made of the rubber resin and be integrally formed with the finger putting portion 74.

The finger putting portion 74 has a coupling recess 76, and the upheaving operation knob 72 is provided with a coupling projection 77 which fits in the coupling recess 76.

In the case of FIG. 14, the finger putting portion 74 may be integrated with the flange member 61.

Next, the operation will be described. When (or after) the operating portion cover 12 is attached to the operating portion 5, the coupling recess 76 of the finger putting portion 74 is coupled (fitted) to the coupling projection 77 of the upheaving operation knob 72.

Figure 16:
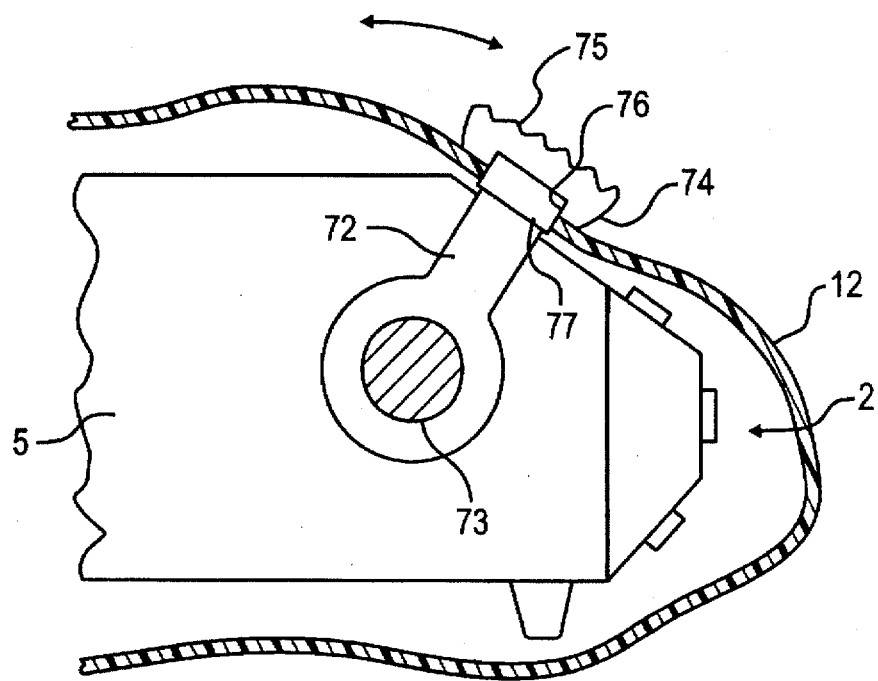
FIG. 16 is a cross-sectional view of an operating portion cover in the vicinity of an upheaving operating knob of a twelfth embodiment of this invention.

The operator can upheave or lower a treating instrument in the direction indicated by the arrows in FIG. 16 usually by putting the thumb of the left hand on the finger putting portion 74 (the left pointing arrow indicates the upheaving direction, and the right pointing arrow indicates the lowering direction). The operating portion cover 12 also moves in response to the operation.

This embodiment has the following effect. Even with the cover attached, the treating instrument can be upheaved and lowered as easily as a conventional endoscope without a cover.

In the foregoing embodiments, the operating portion cover combined with the inserting portion cover is used. However, the foregoing embodiments may apply also to endoscopes which do not have inserting portion covers and only have operating portion covers. As an example of such an endoscope, there is an endoscope in which the joints between parts of the inserting portions are filled with an adhesive to be almost seamless so that the inserting portion can be washed well.

In contrast, the operating portion has some regions where the joints between the parts remain so that the operating portion can be taken apart for maintenance and those regions are difficult to wash. In order to prevent filth from getting into those regions, the abovementioned operating portion cover may be attached to the operating portion during inspection.

Next, referring to FIGS. 17(a) and 17(b), a thirteenth embodiment of this invention will be described. This embodiment is a variation of the structure of the eleventh embodiment and has a grip cover 79 which covers at least a part of an operating portion grip 78, is separate from an operating portion cover 12, and can be attached to and removed from the operating portion grip 78. Although not shown, a part of the grip cover 79 may have uneven portions for preventing slip when gripped.

As shown in FIG. 17(b) which is a plane view seen from the top of FIG. 17(a), the grip cover 79 does not necessarily have to cover the whole grip 78, and it is substantially C-shaped and can be fitted to the grip 78 from both sides thereof.

Control buttons 29 are integrally provided to the grip cover 79 in this embodiment, although the grip cover 79 may be alone without the control buttons 29. As shown in the drawing, there are two control buttons 29, one being a two-step switch for controlling air supply and water supply, and the other being a switch for controlling suction. In order to simplify the operation by removing the two-step switch, three buttons (not shown) may be used for air supply, water supply, and suction, respectively. An electric wire 80 extending from the control buttons is connected to an outside controlling device (not shown) along a universal cord 6 outside the cover.

Next, the operation will be described. Since the operating portion cover 12 is made of a flexible resin, the operating portion cover 12 may slide on the grip 78 therein when the grip 78 is gripped from the outside of the operating cover portion 12, and the feeling of gripping may become worse than that of a conventional endoscope without a cover.

Therefore, the grip cover 79 separate from the operating portion cover 12 is fitted from the side so that the feeling of gripping can be the same as the conventional endoscope.

The same feeling of gripping as that of an endoscope without a cover will be obtained if the grip cover 79 is made of a rigid resin. However, the grip cover 79 may be made of a rubber resin for the purpose of preventing slipping. In case the rubber resin is used, the grip cover 79 may be a cylindrical cover which will cover most of the grip 78, and has a slit. Since it can be easily attached to the grip 78 and can cover most of the grip 78, the feeling of gripping and the external appearance (impression) will also improve.

Because the control buttons 29 are integrally secured to the grip cover 79, the control buttons 29 will be properly positioned with respect to the operating portion 5 and coupled thereto when the grip cover 79 is fitted to the grip 78. As long as the grip cover 79 is gripped, the control buttons 29 will not come off or will not be displaced with respect to the hand gripping it.

The grip cover 79 may be a disposable cover, or a reusable cover which is to be washed and disinfected for repeated use. The grip cover 79 is applicable not only to the eleventh embodiment but also to the first to tenth embodiments.

This embodiment has the effect that a good feeling of gripping can be obtained even from over the operating portion cover 12 made of a flexible material. Further, the grip cover 79 serves also as a means for positioning the externally attached control buttons 29.

Figure 18:
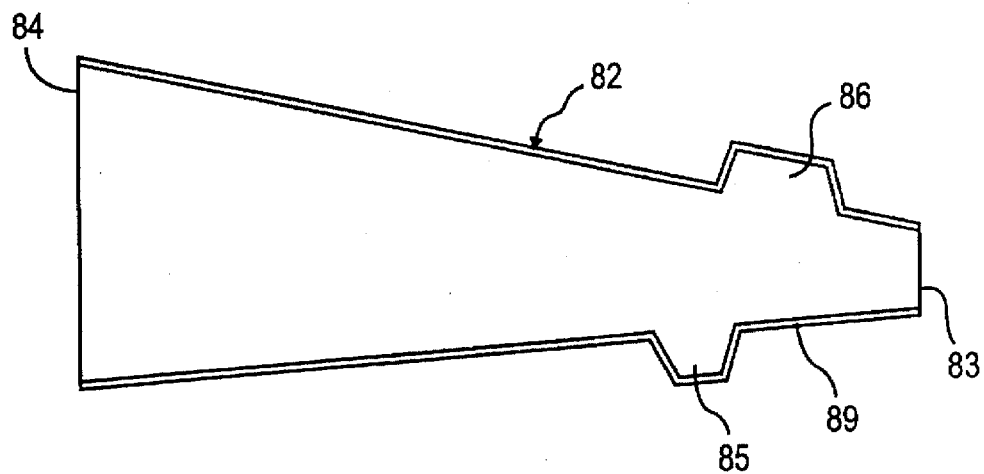
FIG. 18 is a side view of an operating portion cover of a fourteenth embodiment of this invention.
Figure 19:
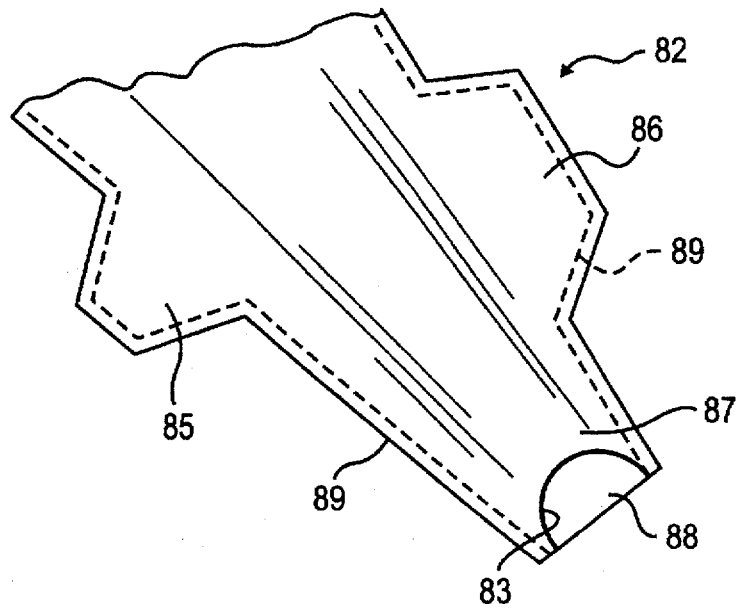
FIG. 19 is a schematic view of the vicinity of the front end portion of the operating portion cover of FIG. 18 seen from almost above.
Figure 20:
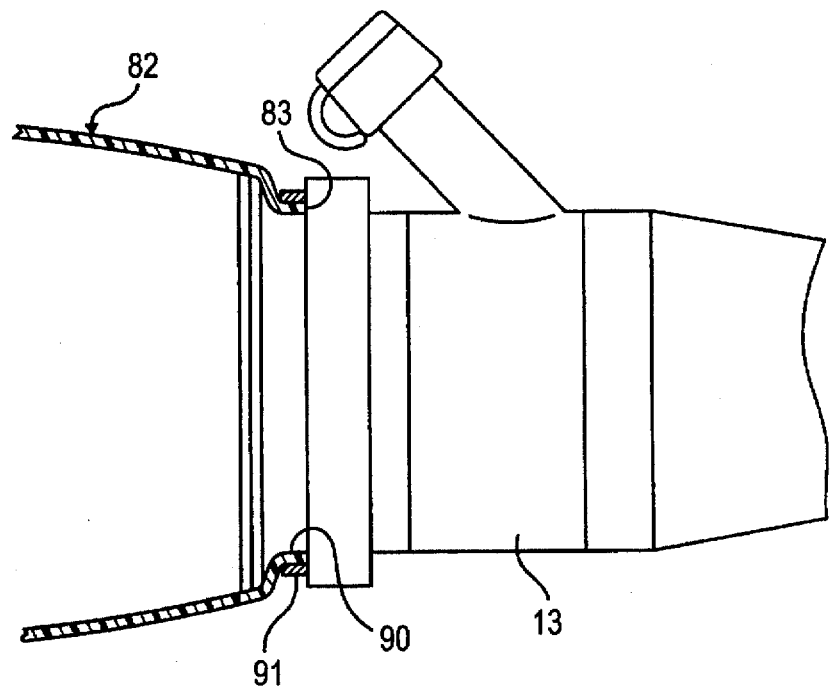
FIG. 20 is a cross-sectional view of the vicinity of a connecting portion between the operating portion cover and a locking cap of the fourteenth embodiment of this invention.
Figure 21:
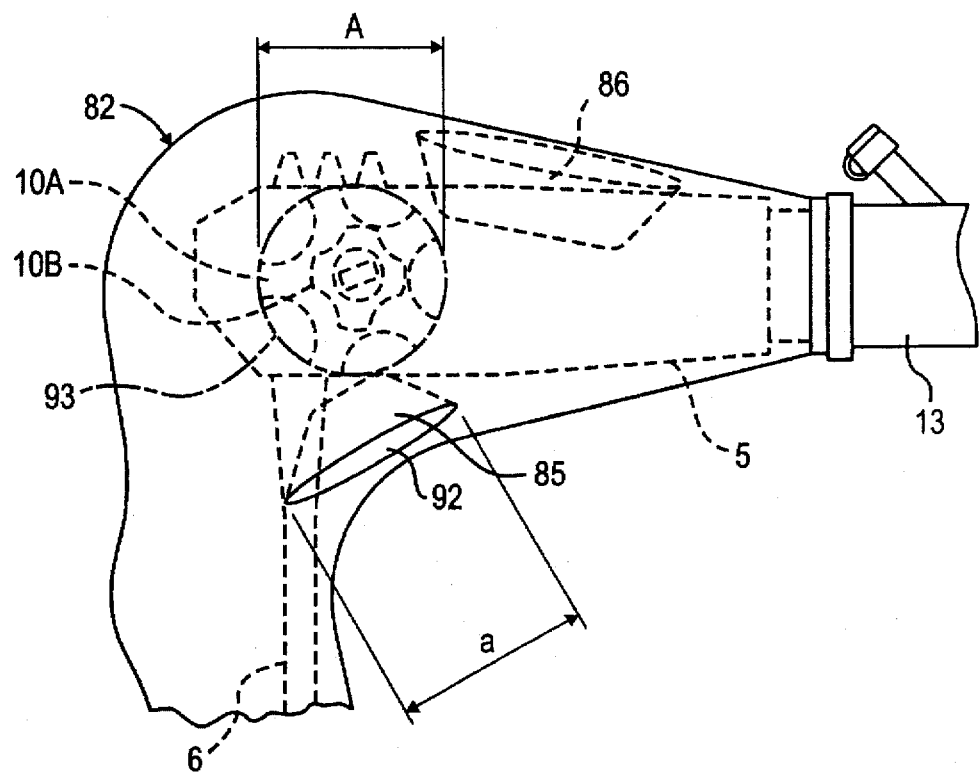
FIG. 21 is a side view of the vicinity of an operating portion of a cover-sheathed endoscope of the fourteenth embodiment of this invention.

Next, referring to FIGS. 18, 19, 20, and 21, a fourteenth embodiment of this invention will be described. FIG. 18 shows a side view of an operating portion cover, FIG. 19 shows a schematic view of the front end portion of FIG. 18 seen from almost above, FIG. 20 shows the connecting portion between a locking cap and the front end portion of the operating portion cover, and FIG. 21 shows the structure in the vicinity of an operating portion of a cover-sheathed endoscope. This embodiment is a variation of the first embodiment.

FIGS. 18 and 19 show an operating portion cover 82 before it is attached to a locking cap 13.

The operating portion cover 82 is substantially cylindrical as a whole, and a front end portion 83 (the right side is the inserting portion side in FIG. 18 et seqq.) and a back end portion 84 are open. As a whole, the operating portion cover 82 is tapered such that the back end portion 84 is wider than the front end portion 83.

The operating portion cover 82 is provided with a pocket 85 (corresponding to the finger putting portion 12a of the first embodiment) and a pocket 86 (corresponding to a combination of the finger putting portions 12b and 12c of the first embodiment) near the front end.

FIG. 19 shows the vicinity of the front end portion 83 and the pockets 85 and 86. The operating portion cover 82 is formed by sticking the edges of sheets 87 and 88 together.

The sheets 87 and 88 have substantially the same shape because their edge portions are connecting portions 89.

The sheets 87 and 88 are connected by welding or gluing at the connecting portions 89 (indicated by bold lines in FIG. 18, and broken lines in FIG. 19). The sheet 87 is substantially larger than the sheet 88, and because they are connected at the connecting portions 89, the sheet 87 is substantially slack when the sheet 88 is laid horizontally. The material of the sheets 87 and 88 is a flexible resin such as polyethylene and vinyl chloride.

The surfaces (especially the inner surfaces) of the sheets 87 and 88 are made uneven by, for example, embossing. Because of such process, the sheets are semi-transparent white if not colored. The surfaces do not always have to be processed unevenly, and they may be processed in other ways if the surface friction resistance will diminish.

FIG. 20 shows a connecting portion of the front end portion 83 of the operating portion cover 82, and the locking cap 13. The back end of the locking cap 13 is provided with a ring-shaped groove portion 90. The front end portion 83 of the operating portion cover 82 is received on the groove portion 90, and wound by an adhesive tape 91.

The adhesive tape 91 may be wound around not only once, but also twice, thrice, or more than that (because the strength increases). The adhesive tape 91 may preferably be unstretchable by, for example, putting cloth in it. Also, a heat contraction tube may be used as the adhesive tape 91.

FIG. 21 shows the operating portion cover 82 attached to an operating portion 5. When the operating portion cover 82 is produced, the pockets 85 and 86 protrude outward, as shown in FIGS. 18 and 19. Then, they are put inside the operating portion cover 82 (only the pockets 85 and 86 are reversed so that they will protrude inwardly).

In FIG. 21, the pockets 85 and 86 are already directed toward the inside of the operating portion cover 82. The width "a" of an opening 92 of the pocket 85 is approximately the same or larger than the width "A" of an operation area 93 of an up-and-down bending knob 10A which is larger than a left-and-right bending knob 10B, so that the whole operation area 93 of the up-and-down bending knob 10A can be easily operated. Therefore, the left-and-right bending knob 10B smaller than the up-and-down bending knob 10A can also be easily operated in its entire operation area.

The distance from the back end of the locking cap 13 to the up-and-down bending knob 10A is substantially equal to the distance from the back end of the locking cap 13 to the opening 92.

Next, the operation will be described.

Since the operating portion cover 82 is generally tapered as shown in FIG. 18, the operating portion cover 82 can be easily attached to and removed from the operating portion 5. Since the operating portion cover 82 is formed by sticking the two sheets 87 and 88 together, it can be made easily by joining the whole connecting portions 89 instantly with an automatic machine, even though it has a complicated shape including the pockets 85 and 86.

Because the sheet 87 has enough slack with respect to the sheet 88, there will be enough clearance in the vicinity of the up-and-down bending knob 10A and the left-and-right bending knob 10B when the cover is attached as shown in FIG. 21, and thus the operating portion cover 82 will be prevented from coiling around the knobs, so that the decline of the efficiency of operation will be prevented.

Because the operating portion cover 82 is semi-transparent (or may be transparent), the shape of the operating portion 5 inside the operating portion cover 82 can be visually recognized as shown in FIG. 21. In FIG. 19, the connecting portion 89 is outside of the operating portion cover 82. However, if the whole operating portion cover 82 is turned inside out so that the connecting portion 89 is directed toward the inner side of the operating portion cover 82, the external appearance will become even better.

Since the inner surface of the operating portion cover 82 is uneven by, for example, embossing, its friction resistance with respect to the operating portion 5 will decrease when the operating portion cover 82 is attached to and removed from the operating portion 5, so that its attachment will be easy.

In FIG. 20, the operating portion cover 82 will not come off from the locking cap 13, because the adhesive tape 91 fixes the front end portion 83 of the operating portion cover 82 by adhesion, and because the adhesive tape 91 and the front end portion 83 are positioned and fixed to the groove portion 90 of the locking cap 13.

Because the adhesive tape 91 is not stretchy, it will not be stretched and come off from the locking cap 13 even when the operating portion cover 82 is pulled from the locking cap 13.

Because the pocket 85 is provided integrally with the operating portion cover 82, the pocket 85 may be difficult to visually recognize. Thus, if the pocket 85 and the opening portion 92 are too small, it will become difficult to recognize their existence, and the operator will have trouble to put his or her thumb in the pocket 85. However, if the size and position of the opening portion 92 is such as shown in FIG. 21, the thumb of the operator gripping the operating portion 5 to operate the up-and-down bending knob 10A will be easily put into the opening portion 92.

Figure 22:
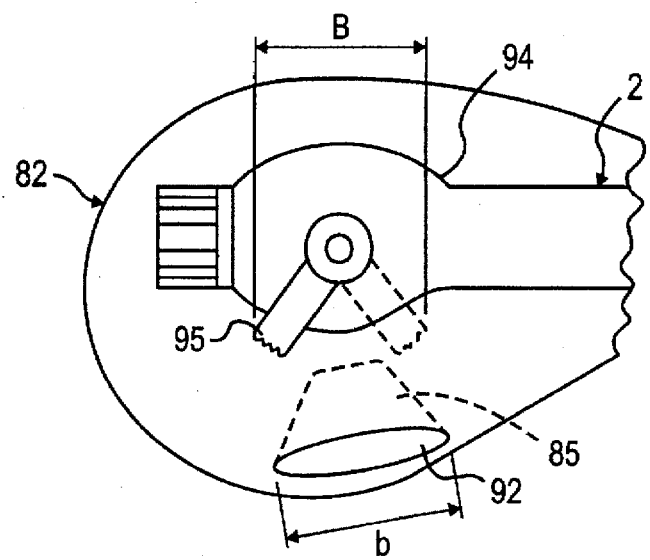
FIG. 22 is a view of the vicinity of an operating portion of a cover-sheathed endoscope of a variation of the fourteenth embodiment of this invention.

FIG. 22 shows a state in which an endoscope with an operating portion 94 having a two-directional bending function is covered. Also here, the width "b" of the opening portion 92 of the pocket 85 of the operating portion cover 82 is substantially equal to or larger than the width "B" of an operation area of a bending knob 95. That is to say, b≧B (the operation is the same as the above-mentioned operation).

Since the opening portion 92 has the above size, the finger of the operator will be easily inserted therein. However, the pocket 85 is tapered as a whole and its top end protruding inward is narrow so that the finger tip of the operator can easily cooperate with the pocket 85 to operate the bending knob as if the operator wears a glove.

This embodiment has the effect that the fingers of the operator can easily be put into the pockets. The other effects are the same as those of the first embodiment. Next, referring to FIG. 23, a fifteenth embodiment of this invention will be described. This embodiment is a variation of the structure of the pocket 85 of the fourteenth embodiment.

In this embodiment, a mark 97 is provided in the vicinity of an opening portion 92 of a pocket 85 by printing or painting. The color of the mark 97 is different from that of an operating portion cover 82.

For example, if the operating portion cover 82 is of semitransparent white, the mark 97 may be black or other colors more noticeable such as red and yellow, or may be luminous. If the operating portion cover 82 is transparent, the mark 97 may preferably be of a color which is not transparent and which is different from the color (usually black) of an operating portion. In any case, the color of the mark 97 is clearly recognizable.

Figure 23:
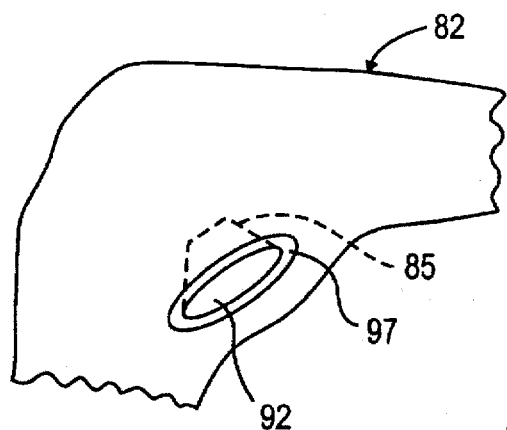
FIG. 23 is a side view of an operating portion cover of a fifteenth embodiment of this invention.

Although the mark 97 is ring-shaped in FIG. 23, the mark 97 is not necessarily ring-shaped and may be of any shape if it will show the position of the opening portion 92.

Further, not only the mark 97 in the vicinity of the opening portion 92, but also the whole pocket 85 may be of a different color from that of the operating portion cover 82. Other structure is the same as that of the fourteenth embodiment.

Next, the operation will be described. The opening portion 92 of the pocket 85 in FIG. 21 is difficult to recognize because the pocket 85 is integrally provided to the operating portion cover 82. However, if the mark 97 is provided in the vicinity portion of the opening portion 92 as shown in FIG. 23, the portion will become recognizable for the operator, so that the operator will be able to easily put fingers for operation into the opening portion 92. Further, if the pocket 85 as a whole is of a different color from that of the cover, the whole pocket 85 will be recognized easily.

This embodiment has the effect that the position of the opening portion 92 of the pocket 85 will be easily recognizable for the operator and fingers will be put into the pocket 85 easily. Other effects are the same as those of the fourteenth embodiment.

Figure 24:
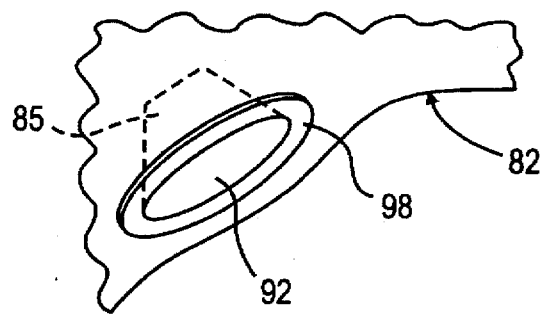
FIG. 24 is a view which shows a structure of the vicinity of a pocket of an operating portion cover of a sixteenth embodiment of this invention.

Next, referring to FIG. 24, a sixteenth embodiment of this invention will be described.

This embodiment is a variation of the fifteenth embodiment. As shown in FIG. 24, a ring member 98 is connected to the periphery of an opening portion 92 of a pocket 85. The ring member 98 is harder (more rigid) than an operating portion cover 82, although it is made of a relatively flexible material such as a rubber resin or other thin resins.

The ring member 98 may also be made of a metallic wire. The ring member 98 remains substantially ring-shaped in its natural state. The ring member 98 is connected to the operating portion cover 82 by welding or gluing. The color of the ring member 98 may preferably be different from that of the operating portion cover 82.

The ring member 98 is not necessarily of a complete ring shape, and may be of any shape which will keep the opening portion 92 open. Also, the shape of the ring member 98 does not have to be a circle, but may be an oval or an ellipse.

The ring member 98 does not have to be a member different from the operating portion cover 82, but may be formed integrally with it. That is to say, the periphery of the opening portion 92 of the operating portion cover 82 may be hardened by heating or the like to keep the opening portion 92 open (such integration could reduce the costs).

The whole pocket 85 may be a member different from the operating portion cover 82, and may be connected to the operating portion cover 82. For example, a finger stall or the like made of a rubber resin may be connected to the opening portion. In this way, not only the opening portion 92 but also the whole pocket 85 will be in an open state.

Figure 17:
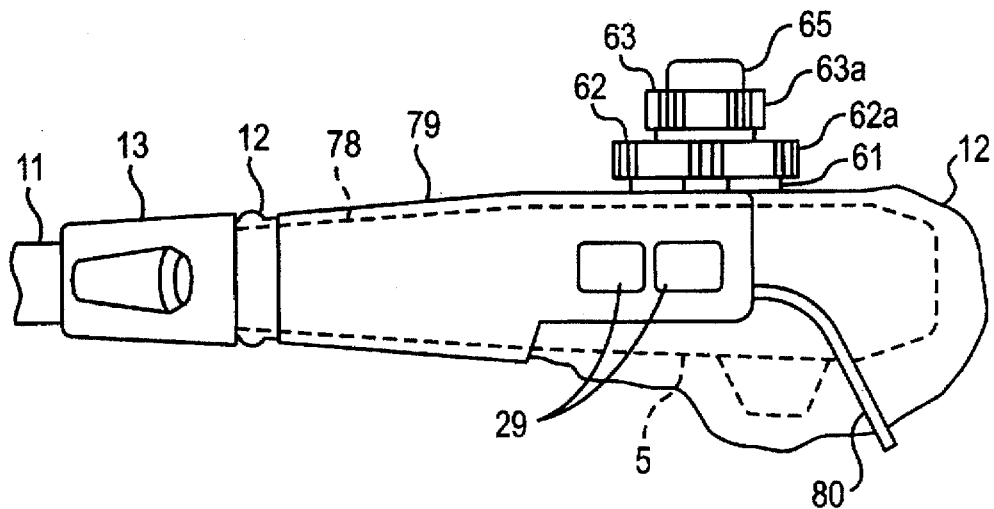
FIGS. 17(a) and 17(b) are side and plane views, respectively, of the vicinity of an operating portion cover of a thirteenth embodiment of this invention.
Figure 17:
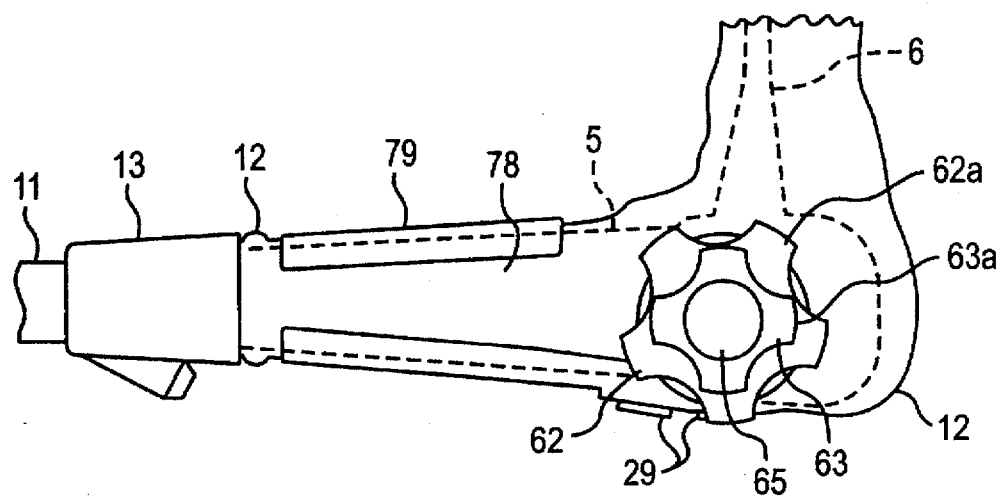

Further, the ring member 98 may be a member different from the operating portion cover 82, and integrated with the grip cover 79 shown in FIG. 17. After the grip cover 79 is attached, the ring member 98 provided integrally with the grip cover 79 is positioned at and fixed to the opening portion 92 of the pocket 85 (because the ring member 98 is integral with the reusable or semidisposal grip cover 79, the costs can be reduced, and fingers may be easily put in because the opening portion 92 will always be maintained at the same position). Other features are the same as the fourteenth embodiment.

Next, the operation will be described.

Because the pocket 85 in FIG. 21 is provided integrally with the operating portion cover 82, if the operating portion cover 82 is wrinkled (it is usually so), the opening portion 92 will not be open and will be difficult to recognize. If the opening portion 92 is not open, even though its position is recognized, the operator will have to put in his or her finger by opening the opening portion 92, which will be troublesome.

In this embodiment, the operator can easily put his or her finger in the pocket 85 because the ring member 98 (or other means) keeps the opening portion 92 open. If the ring member 98 is a different color from that of the operating portion cover 82, it can easily be recognized visually. Further, if the feeling of the ring member 98 is different from that of the operating portion cover 82, the sense of touch of the opening portion 92 will also help the recognition of its position.

Also, if the whole pocket 85 is a finger stall or the like made separately, the fingers can be put deeply into the pocket 85 because not only the opening portion 92 but also the whole pocket 85 are open.

According to this embodiment, it will be easy for the operator to put in his or her finger into the pocket 85. Other effects are the same as the fourteenth embodiment.

Embodiments constructed by combining parts of the above mentioned embodiments are also included in this invention.

What is claimed is:

1. A cover for covering an endoscope having an operating body portion and an operating member provided to the operating body portion, the cover comprising:

an operating body portion cover part for covering at least the operating body portion of the endoscope, the operating body portion cover part having at a predetermined position a first finger putting portion inseparably integrated with the operating body portion cover part and directed toward the inside of the operating body portion cover part for putting a finger wherein the first finder putting portion is formed such that a finger of an operator can be inserted therein.

2. A cover according to claim 1, wherein the finger putting portion is made of a stretchable material.

3. A cover according to claim 2, wherein the stretchable material is a rubber resin.

4. A cover according to claim 1, further comprising a second finger putting portion for putting a finger.

5. A cover according to claim 4, wherein the finger putting portions are for the fingers of a left hand and a right hand, respectively.

6. A cover according to claim 4, wherein the first finger putting portion is on the opposite side from the second finger putting portion with respect to the operating portion.

7. A cover according to claim 1, further comprising means for positioning the first finger putting portion with respect to the operating portion.

8. A cover according to claim 1, wherein the first finger putting portion is rotatable with respect to the operating portion cover part.

9. A cover according to claim 8, wherein the first finger putting portion is made of a rigid material.

10. A cover according to claim 8, wherein the first finger putting portion is made of a flexible material.

11. A cover according to claim 8, further comprising a second finger putting portion for putting a finger, the finger putting portions being rotatable independently of each other.

12. A cover according to claim 1, wherein the operating portion cover part is formed by sticking a plurality of sheets together.

13. A cover-sheathed endoscope comprising:

an endoscope which can be inserted into a living body, the endoscope having an elongated inserting portion, and an operating portion formed behind the inserting portion, the operating portion having an operating body portion and an operating member; and an operating body portion cover part for covering at least the operating body portion of the endoscope;

the operating body portion cover part having at a predetermined position a finger putting portion inseparably integrated with the operating body portion cover part and directed toward the inside of the operating body portion cover part for putting a finger wherein the finger putting portion is formed such that a finger of an operator can be inserted therein.

14. A cover-sheathed endoscope according to claim 13, wherein the operating portion of the endoscope comprises a movable member, and a part of the finger putting portion of the operating portion cover part can be coupled to and removed from a part of the movable member.

15. A cover-sheathed endoscope according to claim 14, wherein the operating portion cover part is folded in the vicinity of the finger putting portion.

16. A cover-sheathed endoscope according to claim 14, wherein the movable member is a bending knob.

17. A cover-sheathed endoscope according to claim 14, wherein the movable member comprises a first bending knob adjacent to the operating portion and a second bending knob smaller than the first bending knob and adjacent to that side of the first bending knob which is away from the operating portion.

18. An endoscope operating portion cover for an endoscope having an inserting portion, an operating body portion coupled to the inserting portion, and an operating member operatively connected to the operating body portion, the operating portion cover being adapted to cover the operating body portion and the operating member and having a large clearance with respect to at least the operating body portion of the endoscope, the operating portion cover comprising a finger putting portion directed toward the inside of the operating portion cover for putting a finger, the finger putting portion being formed as an insertion hole which becomes narrow towards the operating body portion and formed at a position where the clearance is large.

19. An endoscope operating portion cover for an endoscope having an inserting portion, an operating body portion coupled to the inserting portion, and an operating member including a bending knob for bending a distal end portion of the inserting portion, the bending knob having an outside shape, said operating member operatively connected to the operating body portion, the operating portion cover being adapted to cover the operating body portion and the operating member and having a large clearance with respect to at least the operating body portion of the endoscope, the operating portion cover comprising a finger putting portion directed toward the inside of the operating portion cover for putting a finger and formed at a position where the clearance is large.

20. An endoscope operating portion cover according to claim 19, wherein the finger putting portion is formed as a recess corresponding to the outside shape of the bending knob.

21. An endoscope operating portion cover for an endoscope having an inserting portion, an operating body portion coupled to the inserting portion, and an operating member provided to the operating body portion, the operating portion cover being adapted to cover the operating body portion and the operating member and having a large clearance with respect to at least the operating body portion of the endoscope, the operating portion cover comprising a glove portion directed toward the inside of the operating portion cover and formed at a position where the clearance is large.

22. An endoscope operating portion cover according to claim 21, wherein the glove portion can cover up to the vicinity of a wrist of an operator.

23. An endoscope operating portion cover for an endoscope having an inserting portion, an operating body portion coupled to the inserting portion, and an operating member operatively connected to the operating body portion, the operating portion cover comprising:

an operating body portion cover for covering the operating body portion of the endoscope; and an operating member cover for covering the operating member of the endoscope;

wherein the operating body portion cover has a large clearance with respect to at least the operating body portion of the endoscope and is inseparably integrated with the operating member cover; and wherein the operating member cover is rotatable together with the operating member with respect to the operating body portion cover.

24. An endoscope operating portion cover according to claim 23, wherein the operating member cover is rotatable with respect to a rigid flange provided to the operating body portion cover.

25. An endoscope operating portion cover for an endoscope having an inserting portion, an operating body portion coupled to the inserting portion, and an operating member comprising a bending knob for bending a distal end portion of the inserting portion and a braking member for braking the bending knob, said operating member operatively connected to the operating body portion, the operating portion cover comprising:

an operating body portion cover for covering the operating body portion of the endoscope; and an operating member cover for covering the operating member of the endoscope;

wherein the operating body portion cover has a large clearance with respect to at least the operating body portion of the endoscope and is inseparably integrated with the operating member cover.

26. An endoscope operating portion cover according to claim 25, which is adapted to fit to at least a part of the bending knob and formed to have a large clearance with respect to the braking member.

27. An endoscope operating portion cover according to claim 25, wherein the operating member cover comprises a finger putting portion for the bending knob.

28. An endoscope operating portion cover for an endoscope having an inserting portion, an operating body portion coupled to the inserting portion, and an operating member operatively connected to the operating body portion, the operating portion cover comprising:

an operating body portion cover for covering the operating body portion of the endoscope; and an operating member cover for covering the operating member of the endoscope;

wherein the operating body portion cover has a large clearance with respect to at least the operating body portion of the endoscope and is inseparably integrated with the operating member cover, and wherein the operating portion cover further comprises a slip preventing portion.

29. An endoscope operating portion cover for an endoscope having an inserting portion, an operating body portion coupled to the inserting portion, and an operating member operatively connected to the operating body portion, the operating portion cover being adapted to cover the operating body portion and the operating member and having a large clearance with respect to at least the operating body portion of the endoscope, the operating portion cover comprising a pocket portion directed toward the inside of the operating portion cover and formed at a position where the clearance is large and wherein the operating member includes an operation area, and wherein the pocket portion has an opening which is larger than the operation area of the operating member.

30. An endoscope operating portion cover for an endoscope having an inserting portion, an operating body portion coupled to the inserting portion, and an operating member operatively connected to the operating body portion, the operating portion cover being adapted to cover the operating body portion and the operating member and having a large clearance with respect to at least the operating body portion of the endoscope, the operating portion cover comprising a pocket portion directed toward the inside of the operating portion cover and formed at a position where the clearance is large, and wherein the pocket portion has an opening which is provided with an easily visible portion.

31. An endoscope operating portion cover for an endoscope having an inserting portion, an operating body portion coupled to the inserting portion, and an operating member operatively connected to the operating body portion, the operating portion cover being adapted to cover the operating body portion and the operating member and having a large clearance with respect to at least the operating body portion of the endoscope, the operating portion cover comprising a pocket portion directed toward the inside of the operating portion cover and formed at a position where the clearance is large, and wherein the operating portion cover is formed by sticking a plurality of sheet members together.

32. An endoscope operating portion cover for an endoscope having an inserting portion, an operating body portion coupled to the inserting portion, and an operating member operatively connected to the operating body portion, the operating portion cover being adapted to cover the operating body portion and the operating member and having a large clearance with respect to at least the operating body portion of the endoscope, the operating portion cover comprising a pocket portion directed toward the inside of the operating portion cover and formed at a position where the clearance is large, and wherein the operating portion cover further comprises a front end portion on the side of the inserting portion, and a back end portion and is tapered such that the back end portion is wider than the front end portion.

* * * * *